United States Patent
Nozato et al.

(10) Patent No.: US 9,867,538 B2
(45) Date of Patent: Jan. 16, 2018

(54) METHOD FOR ROBUST EYE TRACKING AND OPHTHALMOLOGIC APPARATUS THEREFOR

(71) Applicant: CANON KABUSHIKI KAISHA, Tokyo (JP)

(72) Inventors: Koji Nozato, Rochester, NY (US); Kenichi Saito, Yokohama (JP); Kaishi Ohashi, Tokyo (JP); Akira Sato, Kawasaki (JP); Futoshi Hirose, Yokohama (JP); Hiroshi Imamura, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/076,177

(22) Filed: Mar. 21, 2016

(65) Prior Publication Data

US 2017/0265742 A1 Sep. 21, 2017

(51) Int. Cl.
*A61B 3/14* (2006.01)
*A61B 3/12* (2006.01)
(Continued)

(52) U.S. Cl.
CPC .......... *A61B 3/1225* (2013.01); *A61B 3/0025* (2013.01); *A61B 3/1015* (2013.01);
(Continued)

(58) Field of Classification Search
CPC ..... A61B 3/1225; A61B 3/113; A61B 3/1025; A61B 3/1015; A61B 3/152; A61B 3/0025
(Continued)

(56) References Cited

U.S. PATENT DOCUMENTS 6,421,185 B1 7/2002 Wick et al.
8,045,263 B2 10/2011 Yaroslavsky et al.
(Continued)

FOREIGN PATENT DOCUMENTS

EP 2712542 A1 4/2014
WO 2014023231 A1 2/2014

OTHER PUBLICATIONS

Stephen A. Burns, Remy Tumbar, Ann E. Elsner, Daniel Ferguson, Daniel X. Hammer, Large Field of View, Modular, Stabilized, Adaptive-Optics-Based Scanning Laser Ophthalmoscope, Journal of the Optical Society of America A, Apr. 11, 2007, 24(5): 1313-1326, Optical Society of America, Washington DC, 2007.

(Continued)

*Primary Examiner* — Tuyen Tra
(74) *Attorney, Agent, or Firm* — Canon U.S.A., Inc. IP Division

(57) ABSTRACT

An ophthalmic apparatus includes an AOSLO apparatus, a WFSLO apparatus, and a tracking processor that controls a tracking mirror based on position information calculated from AOSLO and WFSLO images. In another embodiment, the tracking processor controls the tracking mirror based on position information calculated from WFSLO images only. Depending on the amount of movement a target image with respect to a reference image, and the accuracy of detection thereof, the tracking mirror of either the AOSLO apparatus or the WFSLO apparatus can be selectively controlled according to a difference in position of the target image with respect to the reference image.

29 Claims, 8 Drawing Sheets

(51) Int. Cl.
     A61B 3/113   (2006.01)
     A61B 3/00    (2006.01)
     A61B 3/10    (2006.01)
     A61B 3/15    (2006.01)
(52) U.S. Cl.
     CPC ............ *A61B 3/1025* (2013.01); *A61B 3/113* (2013.01); *A61B 3/152* (2013.01)
(58) Field of Classification Search
     USPC ............ 351/208, 206, 205, 200, 45; 396/18
     See application file for complete search history.

(56)                References Cited

U.S. PATENT DOCUMENTS

| | | | |
|---|---|---|---|
| 8,201,943 | B2 | 6/2012 | Hammer et al. |
| 8,444,268 | B2 | 5/2013 | Hammer et al. |
| 8,696,122 | B2 | 4/2014 | Hammer et al. |
| 2009/0275929 | A1 | 11/2009 | Zickler |
| 2010/0253908 | A1 | 10/2010 | Hammer et al. |
| 2013/0215386 | A1 | 8/2013 | Utagawa et al. |
| 2013/0215387 | A1 | 8/2013 | Makihira et al. |
| 2014/0185006 | A1 | 7/2014 | Yonezawa |
| 2014/0240668 | A1 | 8/2014 | Uji et al. |
| 2014/0333749 | A1 | 11/2014 | Imamura |
| 2015/0077706 | A1 | 3/2015 | Yang |
| 2016/0345828 | A1* | 12/2016 | Yang .................... A61B 3/152 |

OTHER PUBLICATIONS

Stephen A. Burns, Remy Tumbar, Ann E. Elsner, Daniel Ferguson, Daniel X. Hammer, Large Field of View, Modular, Stabilized, Adaptive-Optics-Based Scanning Laser Ophthalmoscope, National Institute of Health Author Manuscript, Jul. 8, 2008, PMCID: PMC2443858, U.S. National Library of Medicine, Bethesda MD, 2008.

R. Daniel Ferguson, Zhangyi Zhong, Daniel X. Hammer, Mircea Mujat, Ankit H. Patel, Gong Deng, Weiyao Zou, Stephen A. Burns, Adaptive Optics Scanning Laser Ophthalmoscope with Integrated Wide-Field Retinal Imaging and Tracking, Journal of the Optical Society of America A, Oct. 18, 2010, 27(11):A265-A277, Optical Society of America, Washington DC, 2010.

Qiang Yang, Jie Zhang, Koji Nozato, Kenichi Saito, David R. Williams, Austin Roorda, Ethan A. Rossi, Closed-Loop Optical Stabilization and Digital Image Registration in Adaptive Optics Scanning Light Ophthalmoscopy, Biomedical Optics Express, Aug. 26, 2014, 5(9):3174-3191, Optical Society of America, Washington DC, 2014.

IPIRA office of IP industry research alliances, Accurate and Robust Eye Tracking with a Scanning Laser Ophthalmoscope, Tech ID: 24344 / UC Case 2015-025-0, University of California, Berkeley Office of Technology Licensing—See more at: https://techtransfer.universityofcalifornia.edu/NCD/24344.html, 2015.

* cited by examiner

Frame motion
($X_{n,c}, Y_{n,c}$)

Strip motion
($X_{n,c}, Y_{n,c}$)

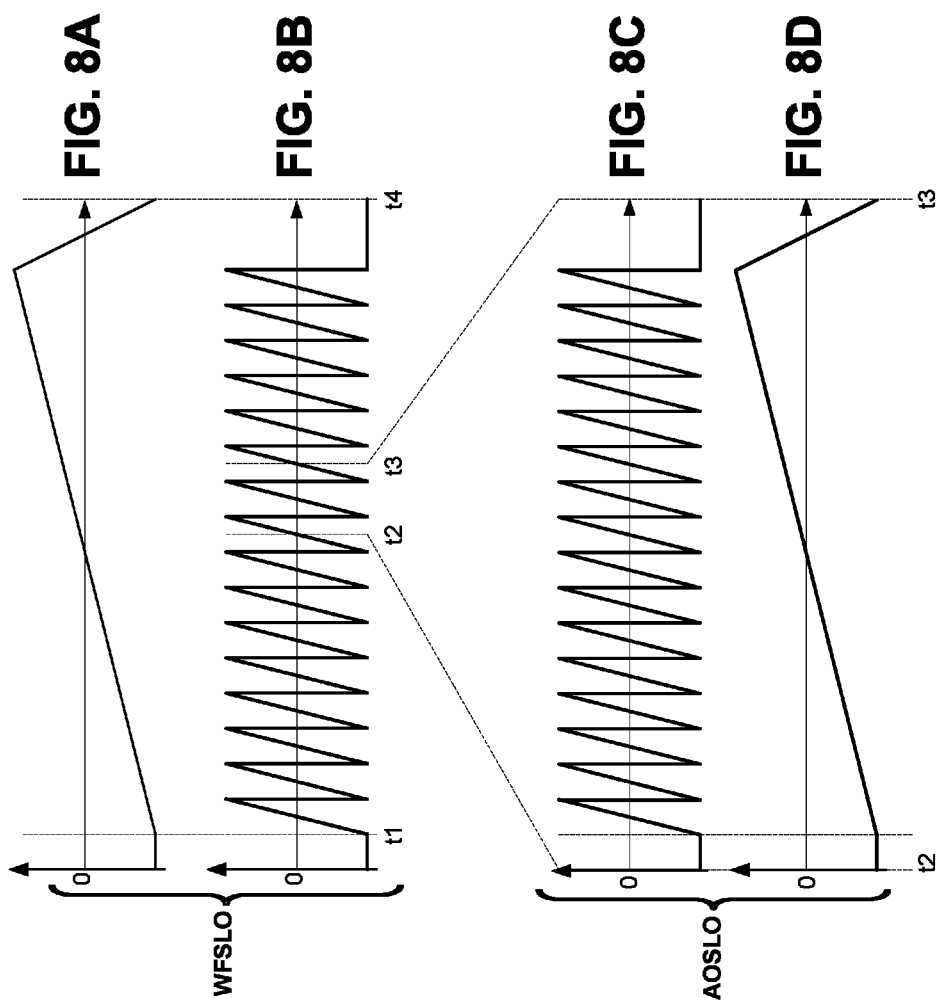

METHOD FOR ROBUST EYE TRACKING AND OPHTHALMOLOGIC APPARATUS THEREFOR

BACKGROUND

Field

The disclosure of this application relates generally to retinal imaging, and more in particular to a method for robust eye tracking and an apparatus therefor.

Related Art

Retinal imaging includes various imaging techniques by which two-dimensional (2D) or three-dimensional (3D) images of the back part of the eye (fundus), which includes the retina, optic disc, choroid, and blood vessels, are obtained. Retinal imaging techniques include, among others, fundus photography, Optical Coherence Tomography (OCT), Scanning Laser Ophthalmoscopy (SLO), and combinations of such techniques which are referred to as multi-modality retinal imaging techniques.

The principle of Optical Coherence Tomography (OCT) is the estimation of the depth at which a specific reflection or backscatter of light originated by measuring its time of flight through interferometry. In retinal imaging, backscatters are typically caused by differences in refractive index in transitions from one tissue layer to another. The backscatter from deeper tissues can be differentiated from backscatter originating at more superficial tissues because it takes longer for the light from the deeper tissues to arrive at the sensor. As the retinal thickness is between 300-500 microns ($\mu$m), the differences in time of flight are very small, but these differences can be measured through interferometry, by applying specialized image processing algorithms. This permits OCT to obtain 2D and 3D images of the retina. Therefore, most retinal layers can be imaged by well known OCT imaging techniques. However, imaging of specific fundus regions, such as the capillary choroid and foveal cones and rods, although available in research laboratory settings, cannot yet be done efficiently and accurately with commercially available devices.

A Scanning Laser Ophthalmoscope (SLO) is a type of confocal microscope which is optimized for imaging specific regions of the fundus of the eye, such as the capillary choroid and foveal cones and rods. SLO imaging is a technique in which image intensities represent the amount of reflected single wavelength laser light obtained in a time sequence. SLO imaging utilizes horizontal and vertical scanning mirrors to scan a specific region of the retina and create raster images viewable on a display monitor. A fundus image is created by scanning a laser beam over the retina of a subject's eye in a raster pattern, and detecting light reflected from each point scanned to electronically produce a digital image. Beam deflection is achieved by a combination of two light-deflecting scanners including one slow vertical scanner (also referred to as "Y scanner") and one fast horizontal scanner (also referred to as "X scanner"). Galvanometer scanners or resonant-type scanners, or even acousto-optic deflectors, are typically used for beam deflection. An appropriate optical detector, such as a photomultiplier tube (PMT) or an avalanche photodiode (APD), is typically used to detect the scanning signal.

In SLO imaging, multiple images are taken in sequence for averaging and constructing a panoramic composite image to analyze the status of an eye. For constructing such panoramic images, each frame in the sequence should be obtained at the exact same location of the eye. But it is very difficult to maintain each frame at the exact same position because an eye naturally moves continuously during imaging. In particular, in small Field Of View (FOV) imaging systems such as an Adaptive Optics SLO (AOSLO), where eye movement is quite large compared with the frame size, the imaging area tends go out of the frame easily due to eye movement. Similarly, in wide FOV imaging systems such as a WFSLO, large eye movements such as a blink tend to prevent accurate imaging even if the imaging area remains within the frame.

To maintain the imaging area within the scanning frame and to correct for involuntary eye movement, SLO tracking techniques have been developed. See, for example patent application publication US 2015/0077706, which discloses an ophthalmoscope including a wide field SLO and a small field SLO for stabilizing the small field SLO against a movement of the eye by use of a tracking mirror controlled by both the small field SLO and the wide field SLO. In addition, patent application publication US 2013/0215386 discloses an ophthalmologic apparatus including a WFSLO apparatus and an AOSLO apparatus where a WFSLO beam and an AOSLO beam enter and scan the fundus simultaneously, so that a stable and high-quality AOSLO image is acquired while the WFSLO apparatus confirms which area of the fundus is being acquired. In these techniques, eye position is detected by a position detection apparatus, and the imaging area is shifted by tracking mirrors according to the eye movement.

The existing technologies of image-based eye tracking for scanning laser ophthalmoscopy are vulnerable to the issue of 'frame out' due to eye drift, where the tracking system stops working or makes incorrect decisions when the eye drifts out of a mapping range of a reference image. To avoid this large motion, a wide field of view retinal imaging system (the WFSLO apparatus) has been proposed to be used for position detection, as mentioned in the above patent application documents.

However, the existing techniques of AOSLO image-based tracking or WFSLO image-based tracking are not stable enough because WFSLO and AOSLO tracking systems typically work independently. Specifically, AOSLO image-based tracking systems can detect only small movement, but it cannot detect large eye motion. On the other hand, WFSLO image-based tracking systems can detect large eye motion, but the position resolution is much lower than an AOSLO tracking system, thus medium sized movements (those larger than the AOSLO resolution but smaller than the WFSLO resolution) may not be detected with enough precision or may not be detected at all.

Therefore, there is a need for improved eye tracking techniques in SLO imaging.

SUMMARY

According to at least one embodiment of the present application, an ophthalmic apparatus includes an AOSLO apparatus, a WFSLO apparatus, and a tracking processor that controls a tracking mirror based on position information calculated from AOSLO and WFSLO images. In another embodiment, the tracking processor controls the tracking mirror based on position information calculated from WFSLO images only. Depending on the amount of movement and the accuracy of detection thereof, the tracking mirror of either the AOSLO apparatus or the WFSLO apparatus can be selectively controlled.

Further features of the present invention will become apparent from the following description of exemplary embodiments with reference to the attached drawings.

BRIEF DESCRIPTION OF DRAWINGS

FIGS. 8A-8B illustrate an exemplary scanning time diagram of a WFSLO apparatus, and FIGS. 8C-8D illustrate an exemplary scanning time diagram of a AOSLO apparatus.

DETAILED DESCRIPTION

Figure 1:
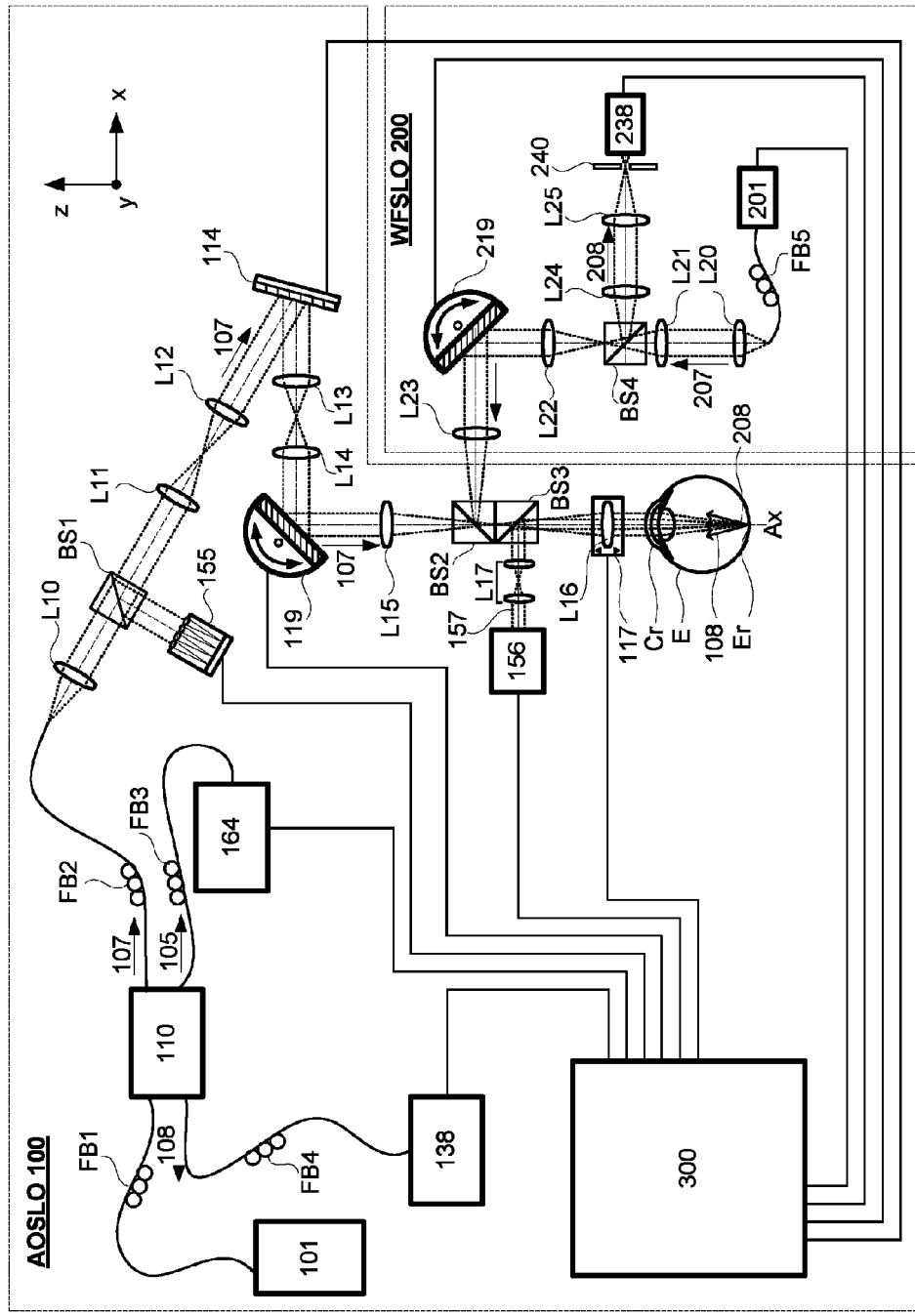
FIG. 1 is a functional diagram that illustrates an exemplary optical arrangement of relevant parts of an ophthalmic apparatus.

In the following description, reference is made to the accompanying drawings which are illustrations of embodiments in which the disclosed invention may be practiced. It is to be understood, however, that those skilled in the art may develop other structural and functional modifications without departing from the novelty and scope of the instant disclosure.

In referring to the description, specific details are set forth in order to provide a thorough understanding of the examples disclosed. In other instances, well-known methods, procedures, components, and circuits have not been described in detail as not to unnecessarily lengthen the present disclosure. Some embodiments of the present invention may be practiced on a computer system that includes, in general, one or a plurality of processors for processing information and instructions, random access (volatile) memory (RAM) for storing information and instructions, read-only (non-volatile) memory (ROM) for storing static information and instructions, a data storage device such as a magnetic or optical disk and disk drive for storing information and instructions, an optional user output device such as a display device (e.g., a monitor) for displaying information to the computer user, an optional user input device including alphanumeric and function keys (e.g., a keyboard) for communicating information and command selections to the processor, and an optional user input device such as a cursor control device (e.g., a mouse) for communicating user input information and command selections to the processor.

As will be appreciated by those skilled in the art, the present examples may be embodied as a system, method, or computer program product. Accordingly, some examples may take the form of an entirely hardware embodiment, and entirely software embodiment (including firmware, resident software, micro-code, etc.) or an embodiment combining software and hardware aspects that may all generally be referred herein as a "circuit", "module", or "system". Further, some embodiments may take the form of a computer program product embodied in any tangible medium of expression having computer-usable program code stored therein. For example, some embodiments described below with reference to flowchart illustrations and/or block diagrams of methods, apparatus (systems), and computer program products can be implemented by computer program instructions. The computer program instructions may be stored in computer-readable media that can direct a computer or other programmable data processing apparatus to function in a particular manner, such that the instructions stored in the computer-readable media constitute an article of manufacture including instructions and processes which implement the function/act/step specified in the flowchart and/or block diagram.

Technical terms used in the context of the present specification have been accorded the ordinary and customary meaning, as understood by persons of ordinary skill in the art to which this application pertains. Certain terms, however, may be accorded a more specific meaning in the context of the present application. For example, the term "light" as used herein generally refers to electromagnetic radiation including not only the visible spectrum, but also the near-infrared (NIR), infrared (IR), and even ultraviolet (UV) ranges of the spectrum.

Exemplary embodiments will be described below with reference to the several drawings. Referring now to the drawings, wherein like reference numerals refer to like parts, an ophthalmic apparatus for obtaining images of an eye of a subject, and methods for performing eye tracking and image reconstruction, are described according to the various embodiments of the present invention.

<Apparatus Optical Overview>

FIG. 1 illustrates an optical overview of an ophthalmic apparatus according to an embodiment of the present invention. As shown in FIG. 1, the ophthalmic apparatus includes the following basic components: an Adaptive Optics Scanning Laser Ophthalmoscope (AOSLO) 100 and a Wide Field Scanning Laser Ophthalmoscope (WFSLO) 200, both operatively connected to various controlling electronics and a computer 300. In FIG. 1, dotted lines represent an optical path, a dash-dot line represents an optical axis, and solid lines represent electrical connections. It is noted herein that although computer 300 is illustrated as a single device for the sake of simplicity, computer 300 corresponds to a combination of control electronics, one or more processors, and one or more computer-readable media coupled to the one or more processors storing programmed instructions (algorithms) that, when executed by the one or more processors, cause the one or more processors to control the ophthalmic apparatus according to the various embodiments of the present invention.

In FIG. 1, coordinates z, x, and y to be used in the following description correspond respectively to an eye axis (or depth) direction, a horizontal direction, and a vertical direction with respect to a fundus image of a retina Er of an eye E. In addition, the x direction corresponds to a main scanning direction, the y direction corresponds to a sub-scanning direction, and the z direction corresponds to an imaging depth direction. Optical elements are exemplary and not limiting, and therefore can be replaced by optically equivalent devices. For example, optical fibers FB1, FB2, FB3, FB4, and FB5 can be replaced by free-space optics.

Similarly, one or more of lenses L10, L11, L12, L13, L14, L15, L16, L17, L20, L21, L22, L23, L24 and L25 may be replaced by mirrors. In particular, in the AOSLO optical path mirrors may be preferable for almost all parts of the optical system between the eye and the Shack-Hartmann sensor because back reflection light from the lens surfaces tend to degrade the accuracy for measuring wavefront aberration.

<AOSLO Apparatus>

As illustrated in FIG. 1, in the AOSLO 100, light emitted from a light source 101 is transmitted to an optical coupler 110 via an optical fiber FB1. The optical coupler 110 splits the light into reference light 105 and measurement light 107. The measurement light 107 is guided to an eye E via a measurement optical path of the AOSLO 100 (AOSLO optical path). As the light source 101 such as, a laser light source, a semiconductor laser, or a super luminescent diode (SLD), can be used. For fundus imaging, the wavelength of the light source to be used is preferably in a range of about 700 nanometers (nm) to 1100 nm. In a practical application, a semiconductor laser having a wavelength of about 780 nm may be used, but an SLD having a wavelength of about 650 to 850 nm would be preferable as laser light tends to generate excessive speckle noise. In particular, if the ophthalmoscope apparatus is to be used for OCT imaging, an SLD light source provides an advantage of having a wide spectral bandwidth.

The reference light 105 split by the optical coupler 110 enters a light intensity sensor 164 through an optical fiber FB3. The light intensity sensor 164 is connected to and controlled by the computer 300 for measuring light intensity of the reference light 105 so as to monitor the light intensity of the measurement light 107. In that regard, in this application, the light intensity sensor 164 may be referred to as a light intensity measuring apparatus. The light intensity of the measurement light 107 is an important parameter in that the intensity should be optimized (kept at a minimum) for the comfort and safety of a subject examinee, while at the same time the intensity should be high enough to ensure high resolution imaging. Examples of an appropriate light intensity sensor 164 include, but are not limited to, a basic PIN photodiode, a photomultiplier tube (PMT), an avalanche photodiode (APD), or the like. It should be noted that measuring the intensity of reference light 105 is only for safety to estimate the light intensity of the measurement light 107 going to the eye. Therefore, reference light 105 and the light intensity sensor 164 can be considered optional. The intensity of measurement light 107 going to the eye may be measured and monitored in a different manner. For example, the intensity of measurement light 107 could be obtained directly from the light source 101.

The AOSLO optical path guides the measurement light 107 from the optical coupler 110 through an optical fiber FB2 to a collimating lens L10. The lens L10 collimates the measurement light 107 into a collimated beam of a desired diameter. The diameter of the measurement light takes into account, both the magnification of the optical system between the collimating lens L10 and the eye, and the entrance pupil diameter of the eye. The entrance pupil diameter of the eye should be about 6~8 mm because of the resolution and subjects' physical limit. To achieve 2~3 micron resolution on the retina, it requires more than a 6 mm entrance pupil size at the subjects' pupil, but the human pupil ranges from about 2 to 4 millimeters (mm) in bright light to about 4 to 8 mm in the dark, for a healthy eye. In addition, sometimes a dilation agent is used to make the subjects' pupil widen to 4 to 8 mm. Therefore, lens L10 collimates the measurement light 107 into a collimated beam of about 4 mm. This is reasonable value because the 4 mm beam is then expanded to 6~7 mm at the pupil of the eye passing through the optical system thereof.

The collimated measurement light 107 is transmitted through a beam splitter BS1 (which may be dichroic mirror) and through relay lenses L11 and L12 to reach a wavefront correction device 114. A reflective liquid crystal spatial phase modulator may be used as the wavefront correction device 114. The reflective liquid crystal spatial phase modulator may include 2 liquid crystal devices, each liquid crystal device may be oriented so as to operate on orthogonal polarizations. A deformable mirror can also be used as the wavefront correction device 114. The measurement light 107 modulated by the wavefront correction device 114 is reflected towards lenses L13 and L14, and enters a mirror of an XY scanner 119 (referred to as the AOSLO XY scanner). Here, it should be noted that the XY scanner 119 is illustrated as a single element for the sake of simplicity of the drawing, but in an actual implementation, two mirrors may be preferable. That is, although it is possible to implement the XY scanner 119 as a single dual-axis scanning apparatus, an AOSLO scanner that includes an X scanner and a Y scanner is preferable in the present application.

The X scanner is a resonance type scanning mirror and serves for scanning the measurement light 107 in a first direction (main scanning direction) perpendicular to the optical axis Ax. The X scanner serves for scanning the measurement light 107 on the retina Er in a first direction (main scanning direction) perpendicular to an optical axis Ax. The first direction or main scanning direction is the x direction which is parallel to the horizontal plane of FIG. 1. The drive frequency of the X scanner is, for example, approximately 7.9 kHz. In FIG. 1, the X scanner of the AOSLO XY scanner 119 can also be used as a tracking mirror, as further explained below.

The Y scanner is a movable mirror for scanning the measurement light 107 in a second direction (sub-scanning direction) perpendicular to the optical axis Ax. The second direction is the y direction which is perpendicular to the plane of FIG. 1. Thus, the second direction is orthogonal to the first direction, and both the first and second directions are perpendicular to the optical axis direction. A galvano scanner is preferably used for the Y scanner. The drive waveform of the Y scanner is a sawtooth wave, and the drive frequency is 64 Hz, with a duty ratio of 16%, for example. Here, it should be noted that the drive frequency and duty ratio of the X scanner and that of the Y scanner are exemplary values, and thus such values are not limiting. However, the drive frequency of the Y scanner is an important parameter for determining a frame rate of the AOSLO images. Therefore, the drive frequency of the Y scanner of the AOSLO should be chosen by taking into account the appropriate frame rate according to the desired application.

Turning back to FIG. 1, after reflecting from the XY scanner 119, the measurement light 107 passes through a lens L15, a dichroic mirror (beam splitter) BS2 and a dichroic mirror (beam splitter) BS3, and is then focused by a focusing lens L16 onto the retina Er of eye E. To that end, the focusing lens L16 is mounted onto a positioning electric stage 117 (electrical translational stage) which is controlled by computer 300 through stage driver electronics. Here, the positional electric stage 117 may be driven by, for example, electro-mechanical or ultrasonic motors controlled by computer 300.

To maintain proper focusing of the measurement light 107, the electric stage 117 is controlled by computer 300 to move the focusing lens L16 in a direction parallel to the optical axis Ax, as indicated by the double arrows. In this manner, the computer 300 controls the electric stage 117 to adjust and control the position of a spot of measurement light 107 at a desired region of the retina Er. Specifically, the position of the focusing lens L16 may be adjusted to thereby condense the measurement light 107 to a predetermined layer of the retina Er of the eye E to observe and image a specific layer of interest. In other words, the positioning electric stage 117 and the focusing lens L16 work as a focusing unit for controlling the measurement light 107 to focus on a region or layer of interest of the eye to be inspected. The driver electronics (shown in FIG. 2) of the electric stage 117, under control from the computer 200, work as a focus control unit for controlling the focusing unit in accordance with an in-focus state of the measurement light 107. In some cases, 2 focusing units may be used for AOSLO and WFSLO separately in each optical system.

The measurement light 107 enters the eye E through the iris thereof and is reflected or scattered by the retina Er. The reflected, fluorescence, or scattered light is referred to as return light 108, which is guided by the AOSLO optical path to the optical coupler 110 in an upstream direction opposite to the above-described downstream direction of measurement light 107. From the optical coupler 110, the return light 108 reaches a detector 138 through an optical fiber FB4. In another example, return light 108 may be divided into 2 beams by a beam splitter (not shown) and a beam is focused on a pinhole sitting just in front of the detector. In this manner, only well corrected return light can pass through the pinhole so that a high resolution confocal image can be obtained. As the detector 138, a high sensitivity optical sensor, for example, an avalanche photo diode (APD), a photomultiplier tube (PMT), or the like can be used.

In the AOSLO optical path, the return light 108 is modulated by the wavefront correction device 114 to correct for optical aberrations caused by the eye. To detect wavefront aberrations, a part of the return light 108 reflected by the beam splitter BS1 enters a wavefront sensor 155. The return light 108 arriving to the wavefront sensor 155 is converted to an electrical signal which is digitized and transmitted to the computer 300. An aberration of the wavefront of the return light 108 caused by structures of the eye E is measured by the computer 300 which is also connected to the wavefront sensor 155. The computer 300 then calculates a modulation amount (wavefront correction amount), on the basis of the wavefront acquired by the measurement result of the wavefront sensor 155, to correct the wavefront of the returning light 108 to that without aberration. To that end, the computer 300 controls the wavefront correction device 114 to perform modulation of returning light 108 according to the wavefront correction amount. The measurement of the wavefront and the wavefront correction via the wavefront correction device 114 can be repeatedly performed under control of computer 300, so that an optimal wavefront is maintained throughout the imaging process. The wavefront correction device 114 includes a reflective liquid crystal spatial phase modulator, but a deformable mirror controlled by MEMS (Microelectromechanical systems) actuators may also apply.

For accurate detection and measurement of the wavefront aberrations, it is necessary that the wavefront sensor 155 and the wavefront correction device 114 are arranged in optically conjugate positions. Indeed, in the AOSLO optical path, the lenses L10 to L16 and all other necessary optics included in the optical path are preferably disposed so that the cornea Cr of the eye E, the XY scanner 119, the wavefront sensor 155, and the wavefront correction device 114 are positioned at optically conjugated planes.

A Shack-Hartmann wavefront sensor (SHWS) and a wavefront curvature sensor are examples of the wavefront sensor 155 which is electrically connected to the computer 300. On the basis of the obtained aberration as a measurement result of the wavefront sensor, the wavefront correction device 114 is controlled in real time by the computer 300 so that the aberration generated in the eye E is corrected each time an AOSLO image is acquired. Therefore, a planar image of the retina Er with appropriate resolution can be acquired.

<WFSLO Apparatus>

In FIG. 1, the WFSLO apparatus 200 has essentially the same basic configuration as that of the AOSLO apparatus 100 except that the WFSLO apparatus does not include the adaptive optics system. In the WFSLO apparatus, light emitted from a light source 201 is guided to the eye E through an optical fiber FB5, lenses L20 and L21, a beam splitter BS4, a collimating lens L22, an WFLSO XY scanner 219, a lens L23, and the already described focusing lens L16.

The light source 201 of the WFSLO apparatus (WFSLO light source) is, for example, an SLD having a wavelength of 910 nm and a bandwidth at full-with half maximum (FWHM) thereof of 10 nm. Here, in order to distinguish the light in the AOSLO optical path from the light in the WFSLO optical path, the AOSLO light source 101 and WFSLO light source 201 emit different wavelengths, and a dichroic mirror (beam splitter) BS2 is used to integrate the two optical paths. In alternative embodiments, the WFSLO apparatus and the AOSLO apparatus may use a common light source or separate light sources with the same or similar wavelengths. In that case, an alternative embodiment may include distinguishing the return light 108 in the AOSLO optical path from the return light 208 in the WFSLO optical path by using pulsed light sources or optical switches to distinguish the light temporally.

In the optical path of the WFSLO (the WFSLO optical path), measuring light 207 emitted from the light source 201 is guided to the eye E through relay lenses L20-L21, the beam splitter BS4, a lens L22, an XY scanner 219, a lens L23, the dichroic mirror (beam splitter) BS2, the dichroic mirror (beam splitter) BS3, and the focusing lens L16. Similar to the AOSLO, the XY scanner 219 of WFSLO (WFSLO XY scanner) includes an X scanner and a Y scanner. The X scanner is, for example, a resonance type scanner for scanning the measuring light 207 on eye E in a main scanning direction perpendicular to the optical axis Ax and parallel to the paper plane of FIG. 1. The drive frequency of the X scanner is, for example, approximately 3.9 kHz. In FIG. 1, the X scanner of the WFSLO XY scanner 219 can also be used as a tracking mirror, as further explained below.

The Y scanner is, for example, a galvano scanner for scanning the measuring light 207 on eye E in a second (sub-scanning) direction perpendicular to the optical axis Ax and perpendicular to the paper plane. The drive waveform of the Y scanner is a saw tooth wave having a frequency of 15 Hz and duty ratio of 16%. The drive frequency of the Y scanner is an important parameter for determining a frame rate of the WFSLO image photography.

FIGS. 8A-8B illustrate an exemplary scanning time diagram of a WFSLO apparatus, and FIGS. 8C-8D illustrate an exemplary scanning time diagram of an AOSLO apparatus. The abscissa in FIGS. 8A to 8D represents time, and the ordinate represents displacements (rotational angles) of the respective scanning mirrors. FIG. 8A shows a signal for the slow mirror (Y scanner) and FIG. 8B shows a signal (saw tooth drive waveform) for the fast mirror (X scanner) of the WFSLO XY scanner 219. On the other hand, FIG. 8C shows a signal (saw tooth drive waveform) for the fast mirror (X scanner) and FIG. 8D shows a signal for the slow mirror (Y scanner) of the AOSLO XY scanner 119. As shown in FIG. 8B, the X scanner of WFSLO XY scanner 219 starts rotating at time t1 and a period for scanning one frame ends at time t4. To illustrate the difference in scanning speeds between the WFSLO XY scanner 119 and the AOSLO XY scanner 219, an interval between time t2 and t3 shows that the AOSLO scanner scans one frame in only a fraction of the period from t1 to t4. Therefore, drive frequency of each of the scanners is an important parameter for determining a frame rate of SLO imaging.

In the WFSLO 200, the beam diameter of the measuring light 207 is preferably about 1 mm, but the beam diameter may be larger than 1 mm or smaller according to the desired parameters of resolution to acquire an optical image of the retina Er. In the WFSLO 200, the measuring light 207 enters the eye Er through the iris thereof and is reflected, fluoresced, or scattered by the retina Er so as to be return light 208. The return light 208 reaches a detector 238 (a high sensitivity sensor) after being transmitted through the focusing lens L16, the dichroic mirror (beam splitter) BS3, reflected from the dichroic mirror (beam splitter) BS2, transmitted through the lens L23, reflected from the WFSLO XY scanner 219, transmitted through lens L22, reflected from beam splitter BS4, and transmitted through relay lenses L24-L25. A beam of the return light 208 may be focused on a pinhole 240 arranged just in front of the detector 238, so that only well corrected return light 208 can pass through the pinhole so that high resolution confocal image can be obtained.

A fixation target 156 which serves to generate a light flux 157 for providing a fixation target to the eye E. The fixation target 156 includes a light-emitting display module (not shown) that has a display surface on an YZ-plane for observation by the eye E. Any one of a liquid crystal array, an organic electroluminescent (EL) display array, and a light emitting diode (LED) display array may be used as part of the display module. During operation of the ophthalmic apparatus, the eye E of a subject examinee receives the light flux 157 from the fixation target 156, and the subject examinee is instructed to observe a displayed target image to fixate or rotate the eye E according to the displayed target image or pattern of images. For example, for fixation a steady (non-moving) image is displayed, and for eye rotation a cross pattern is flashed on the display surface of the fixation target 156 at arbitrarily illuminated positions.

In the fixation target 156, the light flux 157 is guided to the retina Er through a lens system L17; the dichroic mirror BS3 (beam splitter) integrates the light flux 157 with the AOSLO optical path. For appropriate observation, the lenses in lens system L17, and the focusing lens L16 are disposed so that the non-illustrated display surface of the fixation target 156 is optically conjugate with the retina Er. The fixation target 156 is controlled by the computer 300 through driving electronics included in, or connected to, the computer 300.

In operation, the AOSLO apparatus acquires a planar image (AOSLO image) formed by intensities of the return light 108 from the retina Er. The return light 108 as light reflected or scattered by the retina Er enters the detector 138 after passing through the lenses L16 to L10, the wavefront correction device 114, the optical coupler 110, and the like. The light intensity received at the detector 138 is converted into a voltage signal (image signal). The voltage signal obtained by the detector 138 is converted into a digital value by AD circuit 31, and the digital data is passed to the computer 300. The computer 300 performs data processing in synchronization with an operation of the AOSLO XY scanner 119 at the desired drive frequency so as to form the planar image. Here, the reading speed of the AD circuit 31 should be taken into account to allow accurate digital conversion and data transmission. With current technology a read (fetch) speed of about 15 MHz may be appropriate. As noted above, a part of the return light 108 enters the wavefront sensor 155, and hence an aberration of the return light 108 is measured and corrected by the computer 300 operating in synchronization with the wavefront correction device 114.

In operation, the WFSLO 200 acquires a wide field planar image of the retina (WFSLO image) in a manner similar to the AOSLO 100, except that the WFSLO 200 does not use the wavefront sensor or spatial light modulator. To obtain a WFSLO image, the computer 300 controls the XY scanner 119 and acquires intensities of the return light 208 with the detector 238 so as to acquire the wide field planar image of the retina Er. The method of acquiring the wide field planar image of the retina Er (in the plane perpendicular to the optical axis Ax) includes the a process of converting intensity signals into voltage signals, and performing AD conversion and data processing, and in the case of acquiring an AOSLO image, as described above. Here, the computer 300 performs data processing in synchronization with an operation of the WFSLO XY scanner 219 at the desired drive frequency so as to form the wide field planar image. Here, the reading speed of the AD circuit should be taken into account to allow accurate digital conversion and data transmission. With current technology a read (fetch) speed of about 30 MHz may be appropriate. For example, for a scanner having a scanning speed of 15 kHz, 1000 samples/1 fast scanning line*15 kHz scanner(30k line forwards and backwards)=30 MHz. The 1000 sample/line will be decreased to 500 pixels for de-sinusoidal correction.

<Processing Apparatus>

Figure 2:
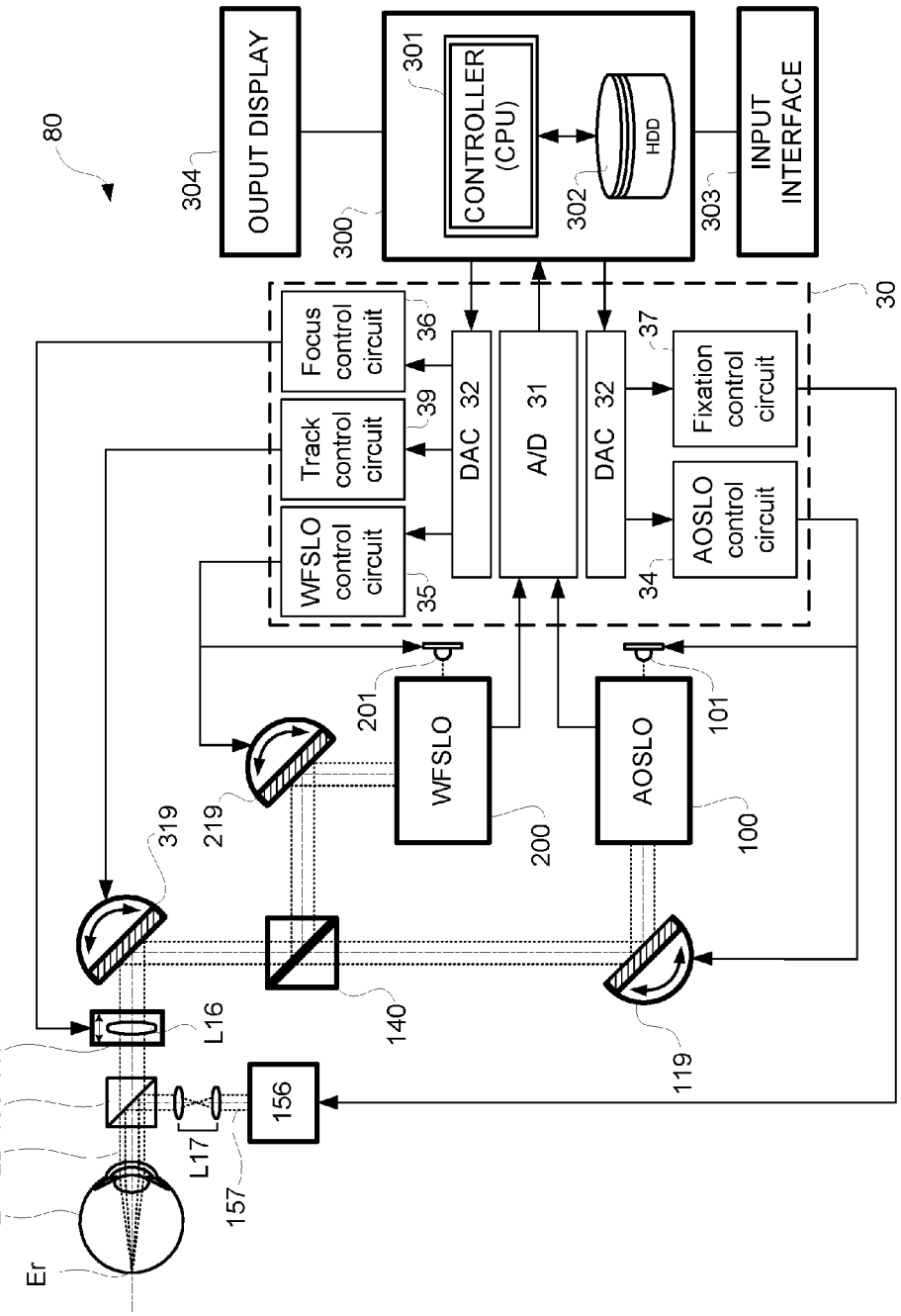
FIG. 2 is a functional diagram that illustrates an exemplary electronic arrangement of relevant parts of an ophthalmic apparatus.

FIG. 2 illustrates a functional overview of the ophthalmic apparatus 80 according to the present invention. In FIG. 2, a processing apparatus corresponds to the computer 300 of FIG. 1. As shown in FIG. 2, the computer 300 includes a controller or central processing unit (CPU) 301 for controlling functional members of the ophthalmic apparatus 80. In addition, computer 300 includes a storage memory HDD 302, a user interface 303, and output display 304, and input/output circuitry, represented by a controller circuit 30, necessary to operate and control the various parts of the ophthalmic apparatus 80. In FIG. 2, dotted lines represent an optical path, a dash-dot line represents an optical axis, and solid lines with arrows represent electrical connections.

Similar to FIG. 1, the functional diagram of FIG. 2 shows the ophthalmic apparatus 80 includes the Adaptive Optics Scanning Laser Ophthalmoscope (AOSLO) 100 and the Wide Field Scanning Laser Ophthalmoscope (WFSLO) 200 operatively connected to controller circuit 30, which in turn is connected to computer 300 (processing apparatus). The AOSLO 100 includes light source 101, and the WFSLO 200 includes light source 201 separate from light source 101. The AOSLO 100 guides light of a first wavelength from its light source 101 to an eye E via the AOSLO optical path. Similarly, the WFSLO 200 guides light of a second wavelength from its light source 201 to the eye E via the WFSLO optical path. At least part of the AOSLO optical path and part of the WFSLO optical path overlap each other, as described and shown in reference to FIG. 1. Therefore, a dichroic mirror (beam splitter) 140 is used to integrate the light at the point where the two optical paths meet. In this manner, each of the AOLSO 100 and the WFSLO 200 scans the retina Er of the eye E with a light beam LB transmitted through focusing lens L16. The focusing position of the light beam LB on the retina Er is controlled by the positioning electric stage 117. The scanning position of the light beam LB on the retina Er is controlled by scanning mirrors of the AOSLO XY scanner 119 and the WFSLO XY scanner 219, as described in reference to FIG. 1. In FIG. 2, a tracking mirror 319 is used for eye movement tracking and optical stabilization, according to an embodiment of the present invention.

A fixation target 156 transmits a fixation light flux 157 (fixation pattern or image) through the lens system L17; and a dichroic mirror 158 (corresponds to BS4 in FIG. 1) integrates the fixation light flux 157 with the optical path of light beam LB. In operation, a subject being examined is given a fixed target (image or light pattern) to stare at, so that motion of eye E is avoided. Alternatively, the subject may be instructed to visually follow a fixation target in a predetermined direction.

The AOSLO apparatus (AOSLO 100) may be implemented as a catadioptric optical system (a combination of both reflective and refractive optical elements), as shown in FIG. 1, or as a purely reflective optical system. An all-reflective AOSLO system may be advantageous in limiting back reflections and minimizing chromatic aberrations, but optical alignment may be difficult. In contrast, a catadioptric AOSLO system may be advantageous in facilitating ease of arrangement (e.g., aligning) of refractive elements (lenses) while limiting back reflections and minimizing chromatic aberrations with reflective elements (mirrors). The AOSLO 100 may use plural telescopes consisting of conjugate pairs of spherical or aspherical mirrors (or lenses) to relay light from the AOSLO light source 101 to a plane conjugated with the pupil of the eye E. In the AOSLO 100, at least one pair of scanning mirrors including one fast scanning mirror (first axis mirror) and one slow scanning mirror (second axis mirror) are necessary for raster scanning a spot of light across the retina Er of the eye E. The light reflected from the retina Er is relayed to a wavefront correction device 114, and subsequently detected by the wavefront detector 155 (e.g., Shack Hartmann wavefront sensor).

The WFSLO apparatus 200 may be arranged in series or in parallel with the AOSLO 100. Similar to the AOSLO, the WFSLO 200 may be implemented as a catadioptric system (a combination of both reflective and refractive optical elements), or as an all-reflective optical system. The WFSLO 200 can be similarly configured to use plural telescopes made of pairs of spherical or aspherical mirrors (or lenses) and dual-axis scanners (e.g., galvanometer mirrors) to relay light from the light source 202 to a plane conjugated with the pupil of the eye E, and thus raster scan a spot of light across the retina Er. In contrast to the AOSLO 100, the WFSLO 200 requires neither a wavefront corrector nor a wavefront detector. Instead, the WFLSO 200 may use a high-sensitivity sensor such as an avalanche photodiode or a photomultiplier tube (PMT). The WFSLO 200 is primarily used as a real-time tracking and/or feedback system for the AOSLO 100. Similarly, AOSLO 100 is also used as a real-time tracking and/or feedback system for the WFSLO 200. In this manner, the AOSLO image-based tracking can precisely detect small movements of the eye, and the WFSLO image-based tracking can detect large movements of the eye, thereby ensuring that both large and small movements of the eye are tracked and corrected in real time, so that high resolution images of even small regions of the retina can be obtained at the exact same position.

Light reflected, fluoresced, or scattered from the retina Er is converted to an analog voltage by a high sensitivity light sensor included in each of the AOSLO 100 and WFSLO 200, as described above. Signals from each of the AOSLO high sensitivity sensor (detector 138) and from the WFSLO high sensitivity sensor (detector 238) are sent to an electronics circuit 30 and digitized with an analog-to-digital (A/D) converter, which is shown as A/D circuit 31 in FIG. 2. The A/D circuit 31 sends the digitized signal (data) to the computer 300. In the computer 300, a non-illustrated graphics processing unit (GPU) executes data processing, and then the CPU 301 performs a tracking process/algorithm (see below for details) to calculate eye motion. The computer 300 sends the calculated eye motion data to digital-to-analog converters (DAC), shown in FIG. 2 as DAC circuit 32. The DAC 32 converts digital eye motion signals (eye motion data) back to analog voltage signals. The analog voltage corresponding to the eye motion is sent by an AOSLO control circuit 34 to a fast scanning mirror of the AOSLO XY scanner 119. Alternatively or in addition thereto, the analog voltage corresponding to the eye motion is sent by a WFSLO control circuit 35 to a fast scanning mirror of the WFSLO XY scanner 219. Furthermore, the analog voltage corresponding to the eye motion is sent by a track control circuit 39 to tracking mirror 319. In response to the received voltage signal the tracking mirror 319 selectively adjusts (moves) the position of the light beam LB on the retina Er to negate the effect of the eye motion.

In FIG. 2, tracking mirror 319 and its corresponding track control circuit 39 is an example of how eye tracking can be implemented. However, it is contemplated that eye tracking can be implemented in various arrangements. In one embodiment, as shown in FIG. 1, tracking may be done by adjusting the scanning signals sent to the scanning mirrors of the WFSLO XY scanner 119 and/or the AOSLO XY scanner 219. Alternatively, tracking may be done with the use of one or more specialized tracking mirrors. For example, as shown in the arrangement of FIG. 2, the tracking mirror 319 may make use of one or more tracking mirrors to adjust the scanning position of the beam LB. In an alternative embodiment, one or more of the AOSLO apparatus 100 and/or WFSLO apparatus 200 may include their own (dedicated) tracking mirror 319. The tracking mirror 319 may be implemented as any one of, a tip-tilt mirror, a combination of orthogonal mirrors, or a combination of large stroke and small stroke mirrors. In addition, it should be noted that although FIG. 2 shows the AOSLO XY scanner 119 and the WFSLO XY scanner 219 as single elements, each includes an X scanner and a Y scanner.

As an example of the electronics circuit 30, a field programmable array (FPGA) device (e.g., ML506, Xilinx Inc., San Jose, Calif.) may be employed to control data acquisition from the AOSLO sensor (detector 138) and from the WFSLO sensor (detector 238), and to program the DAC 32 for driving the tracking mirror of XY scanners 119 and 219. The A/D circuit 31 may be implemented as an integrated circuit (chip) residing on the FPGA for image acquisition, and the D/A conversion may be performed with one or more dedicated DAC circuits (e.g., 125 MSPS 14-bit, DAC2904EVM, Texas Instruments Inc., Dallas, Tex.). The tracking algorithm may run directly on the CPU 301 of computer 300 or it may run on a consumer-level graphics processing unit (GPU), for example, NVIDIA® GTX560, by NVIDIA Corporation, of Santa Clara, Calif. The GPU may be integrated within the computer 300, or may arrange separately from, but in operative communication with, the computer 300.

The CPU 301 outputs data to the AOSLO 100 and the WFSLO 200 via an output circuit corresponding to DAC 32. The output display 304 is, for example, a LCD display monitor and serves to display the acquired images, the calculated results, and various instructions to a user of the ophthalmic apparatus 80. The user interface 303 includes various computer peripherals such as a pointing device (mouse), a keyboard, and the like, which are useful for an operator to operate the imaging functions of the ophthalmic apparatus.

<Image Processing>

As noted in the Background section of this specification, in SLO imaging, multiple images are taken for averaging and constructing a panoramic composite image to analyze the status of an eye. For constructing such panoramic images, each frame should be at the exact same position. However, since it takes time to scan each image, involuntary eye movement such as microsaccades, blinks, or inadvertent head movement (head turning or shaking) represents a major hindrance to efficient SLO imaging even during careful fixation. Therefore, it remains highly desirable to minimize, compensate, and/or eliminate eye motion.

In SLO imaging, each frame is constructed by raster scanning the retina Er repeatedly and registering (recording) the images on a frame by frame basis. In the scanning process, the frame rate at which images are recorded is given by the ratio of the scan velocity to the spot size. Since current SLO scanners can reach very high scanning rates, the scanning frequency does not represent a major issue. The spot size is determined based, among other factors, (a) the desired resolution of the image to be acquired, (b) the scan aperture which in a human subject is determined by the pupil diameter of the subject's eye, and (c) the scanning angle of the light beam. For high resolution images, as in the case of AOSLO images, frame rates as high as 21 fps (frames per second) have been achieved. On the other hand, for WFSLO images, frame rates of about 15 fps have been reported.

At these frame speeds, in addition to the scanning time, electronic latencies in reading and registering (storing) image data also contribute to the difficulty of constructing accurate planar images. Specifically, although each frame can be obtained in a fraction of a second, when processing frame by frame, the processing apparatus requires time for data acquisition, time for data buffering, time for image preprocessing (e.g., denoising), and time for calculating eye motion between successive frames. Therefore, it becomes more difficult to accurately track and correct eye motion, in particular in high resolution AOSLO imaging, and when changing imaging mode from high resolution AOSLO imaging to lower resolution WFSLO imaging, and vice versa.

Figure 3:
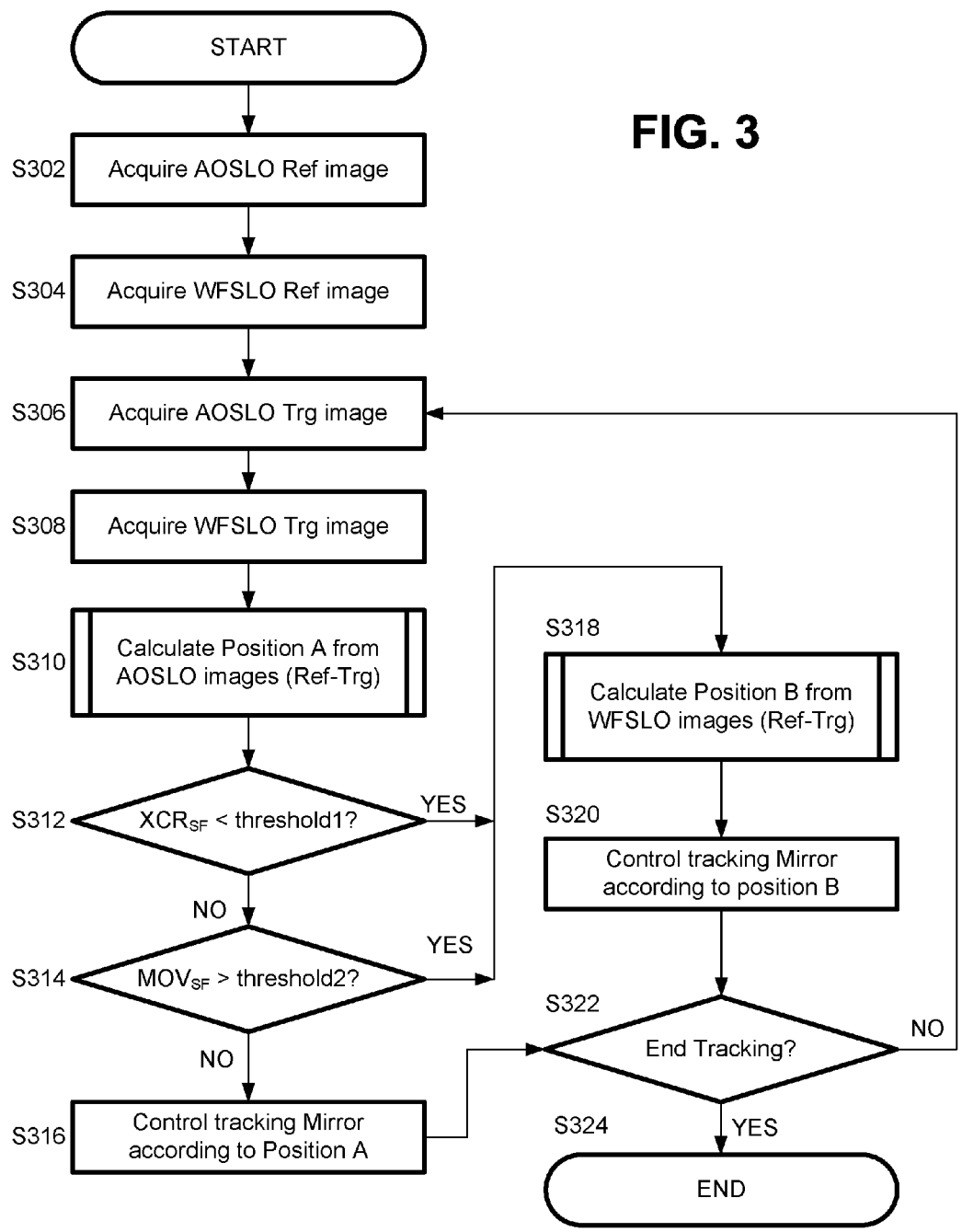
FIG. 3 illustrates a flow process performed for eye movement tracking and optical stabilization, according to a first embodiment of the present invention.
Figure 4:
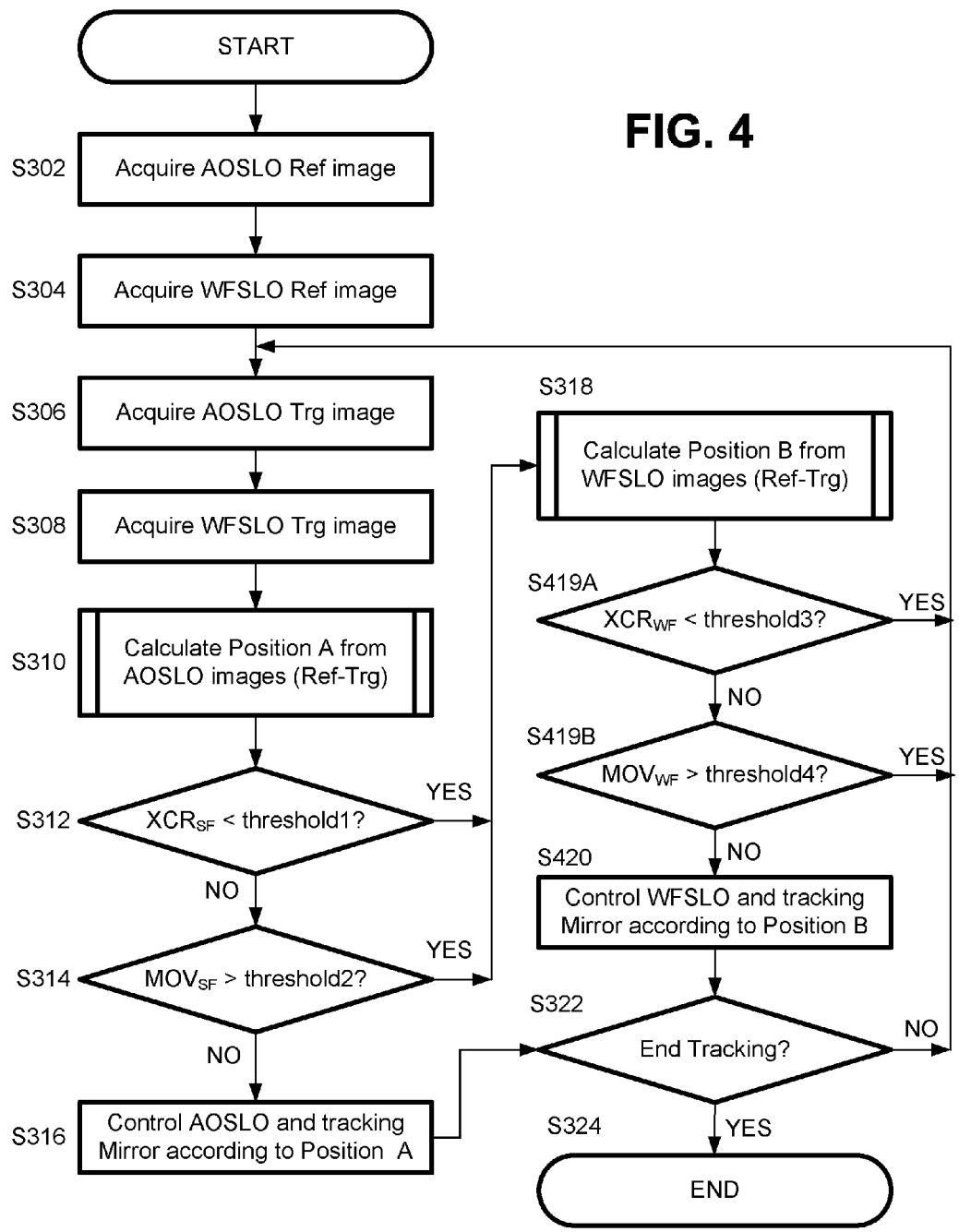
FIG. 4 illustrates a flow process performed for eye movement tracking and optical stabilization according to a first modification of the embodiment shown in FIG. 3.
Figure 5:
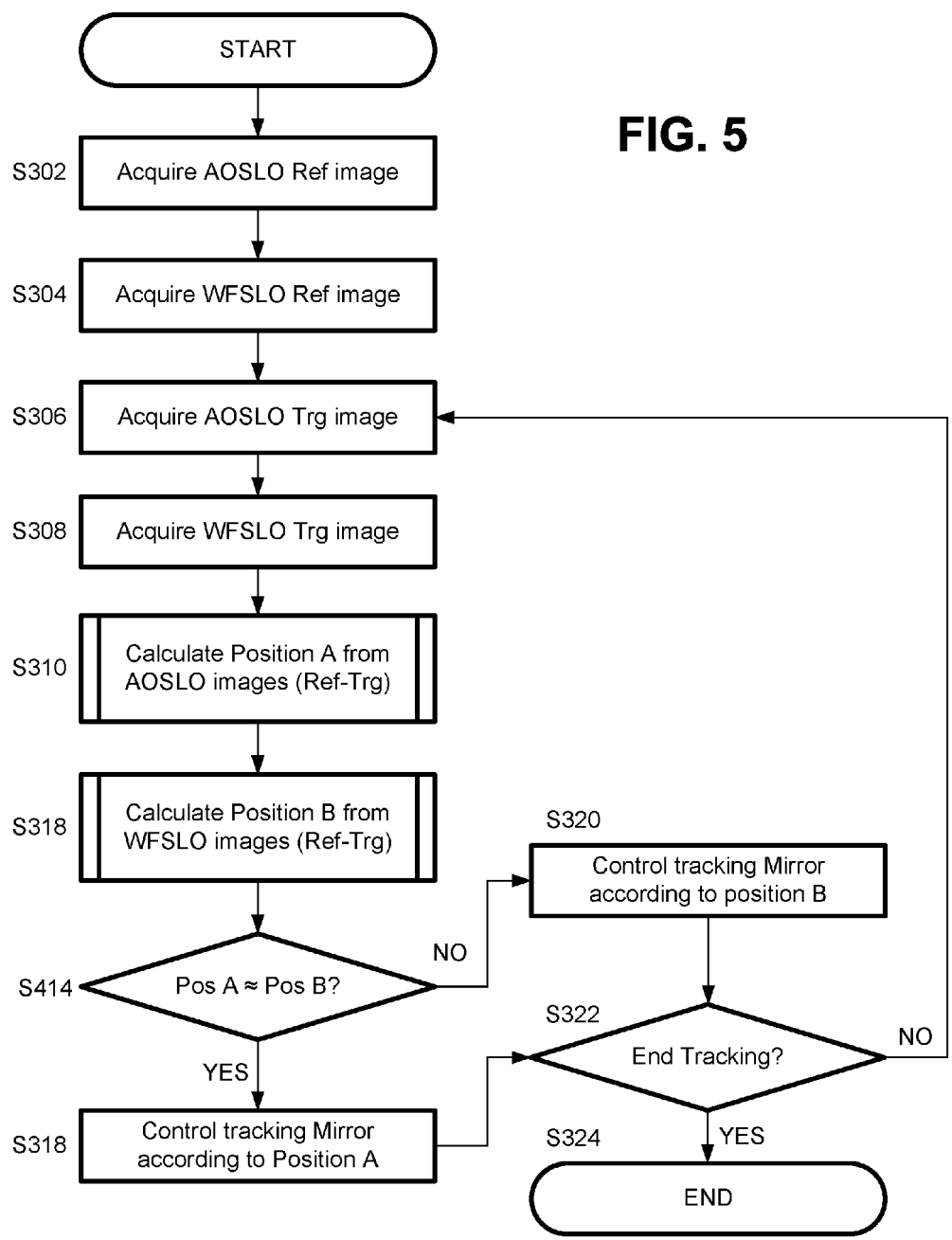
FIG. 5 illustrates a flow process performed for eye movement tracking and optical stabilization according to a second modification of the embodiment shown in FIG. 3.
Figure 7:
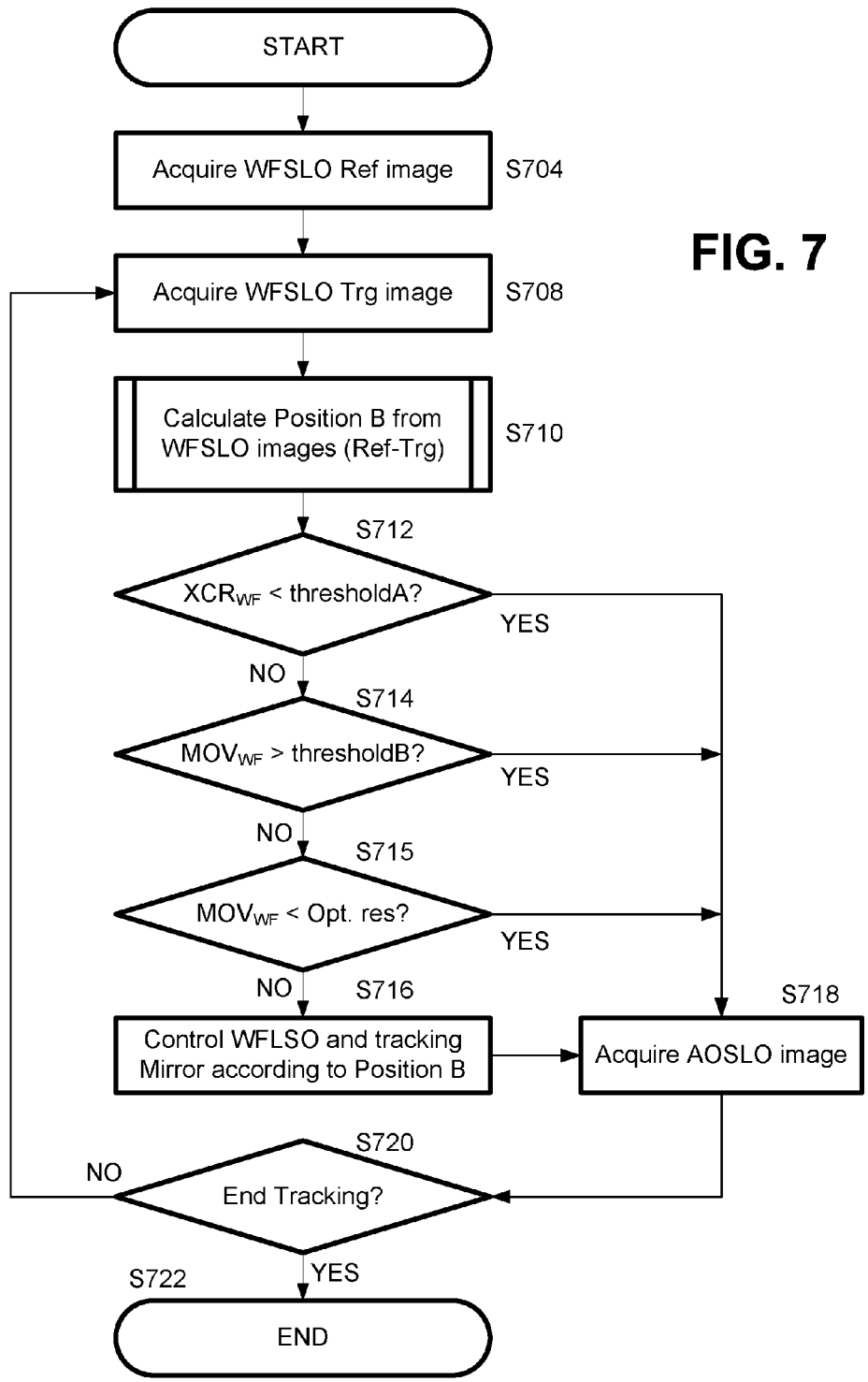
FIG. 7 illustrates a flow process performed for eye movement tracking and optical stabilization, according to a second embodiment of the present invention.

Therefore, according to the present invention, the following process is performed to improve tracking and optical stabilization in SLO retinal imaging. The process of acquiring AOSLO images and WFSLO images while performing eye tracking and optical stabilization is now described herein below, according to the flow of FIGS. 3, 4, 5 and 7, by referring to the functional diagram of FIG. 2 and the optical diagram of FIG. 1. FIGS. 3-5 illustrate a flow process performed for eye movement tracking and optical stabilization in which a processing apparatus (processor or CPU) controls a tracking mirror according to whether a difference in position of a target AOSLO image with respect to a reference AOSLO image, or a difference in position of a target WFSLO image with respect to a reference WFSLO image, meets certain conditions. FIG. 7 illustrates a flow process performed for eye movement tracking and optical stabilization in which a processor controls a tracking mirror according to whether a difference in position of a target AOSLO image with respect to a reference AOSLO image matches a difference in position of a target WFSLO image with respect to a reference WFSLO image. The process begins at a START state in which the ophthalmic apparatus 80 is placed in an operating state (i.e., in an ON state).

In FIG. 3, at step S302, once the ophthalmic apparatus is in operational state, computer 300 controls the AOSLO apparatus (AOSLO 100) to acquire a first AOSLO image, which is referred-to herein as a "reference AOSLO image". To that end, an operator or user of the ophthalmic apparatus 80, via an input device (user interface 303), first selects and enables (turns ON) a display element (e.g., an LED or an array thereof) constituting the fixation target 156. When a subject under examination stares at the turned-on fixation target 156, the eye E is expected to be fixated to a stable position. The foregoing is referred to as a fixation operation. In this state, the AOSLO light source 101 is turned ON preferably in a state in which the AOSLO XY scanner 119 is stopped (not yet scanning). The AOSLO beam of measurement light 107 emitted from the light source 101 irradiates the eye E, and light is reflected, fluoresced, or scattered by the fundus layers of the retina Er, as return light 108. The return light 108 returns through the AOSLO optical path and enters the wavefront sensor 155. The CPU 301 of computer 300 controls drive electronics (circuit 30) to drive the wavefront correction device 114 based on the light that has entered the wavefront sensor 155, and thus the CPU 301 corrects any wavefront aberration caused by eye, by modulating the return light 108.

Next, the computer 300 (or the user) activates the AOSLO XY scanner 119 to raster scan a desired area of the retina Er of eye E with the AOSLO beam of measurement light 107. Then, return light 108 scattered or reflected from the retina Er travels to the detector 138 (a high sensitivity light intensity sensor) where the return light is photoelectrically converted into a voltage signal. The CPU 301 of computer 300 controls the electronic circuit 30 to acquire an image signal (voltage signal) from the AOSLO sensor (detector 138) via A/D circuit 31. The CPU 301 receives digital signals from A/D circuit 31, generates the first AOSLO image, and stores such image as the AOSLO reference image in the storage memory HDD 302. Here, the AOSLO reference image is generated by an image processor which can be implemented either by CPU 301 or by a separate GPU mounted on or connected to computer 300.

At step S304, the computer 300 controls the WFSLO apparatus (WFSLO 200) to acquire a first WFSLO image, which is referred-to herein as a "reference WFSLO image". To that end, the fixation operation continues to be performed so that the eye E continues fixed in the same position where the reference AOSLO image was stored. In this state, the WFSLO light source 201 emits light (laser light), as measurement light 207, which is guided to the eye E via the WFLSO optical path, which was described above with reference to FIG. 1. Upon scanning the retina Er, return light 208 reflected, fluoresced, or scattered from the retina Er travels back via the WFSLO optical path and is received by the detector 238 to acquire the first WFSLO image. Here too, the computer 300 activates the WFSLO XY scanner 219 to raster scan the retina Er of eye E with the WFSLO beam of measurement light 207, and return light 208 from the retina Er is photoelectrically converted by the light detector 238.

Then the CPU 301 of computer 300 controls the circuit 30 to acquire an image signal (voltage signal) from the WFSLO sensor (detector 238) via the A/D circuit 31. At his point, the image processor (CPU 301 or a separate GPU) generates the first WFSLO image and stores such image as the reference WFSLO image in the storage memory HDD 302.

Here it is contemplated that the reference AOSLO image and the reference WFSLO image may be generated from one or more frames. In the case that two or more frames are used to generate the reference image, such frames are averaged and denoised so that a reliable reference image is acquired and stored. In addition, the order in which the AOSLO reference image and the WFSLO reference image are acquired and stored in storage memory HDD 302 is not relevant. As long as the references images are stored prior to acquiring the below described "target" images, the reference images could be acquired in any order. However, to minimize discomfort to the subject being examined and avoid eye movement, the reference AOSLO image and the reference WFSLO image may be acquired simultaneously, or one after another in a relatively short succession.

At step S306, a target AOSLO image is acquired in the same manner as described in step S302. At step S308, a target WFSLO image is acquired in the same manner as described in step S304, except that the storing of target images may be optional. Specifically, the CPU 301 can be programmed to generate a target image (target AOSLO image or target WFSLO image) from a single frame or a part of a frame (e.g., a strip of a frame). To minimize electronic latency, the CPU 301 can be programmed to hold the target image in temporary memory, so that the target image is not registered (stored permanently) in storage memory HDD 301 until the position of the target image with respect to that of the reference image is considered acceptable. For that reason, the target images can be temporarily stored, for example, in a non-illustrated volatile random access memory (vRAM).

At step S310, once the target images have been acquired, the CPU 301 calculates the position of the target AOSLO image with respect to the position of the reference AOSLO image. Specifically, at step S310, the CPU 301 calculates a relative position (a difference in position) of the target AOSLO image with respect to the position of the reference AOSLO image (herein "position A"). The manner in which the CPU 301 calculates the position (position information) of the target images with respect to the reference images is discussed below in more detail.

Here, eye motion and therefore a difference in position between the reference image and target image can be calculated according to known tracking algorithms. For example, a difference in position of the images based on a cross-correlation of the reference image and the target image can be used. As it is known, in signal processing, cross-correlation is a measure of similarity of two time-dependent signals as a function of the lag of one relative to the other. In image processing, on the other hand, one approach for identifying dissimilarities between a reference image and a target image uses cross correlation of the target image with a suitable mask or reference image by detecting a pattern or feature within a target image. Notably, when the reference image and the target image have a similar feature or pattern, and such feature or pattern overlap, the cross correlation will be high. Therefore, the reference image needs to have the same functional appearance as that of the target image. In this manner, when the reference image overlaps at every pixel with the target image and the cross correlation is calculated, a 2D array of correlation coefficients is generated. This means that a position of a given pattern or feature is determined by a pixel-wise comparison of the target image with a given reference image that contains the desired pattern or feature. Therefore, cross correlation calculation is a computationally intensive process.

A cross-correlation coefficient (herein "XCR") of 1 (also known as auto correlation) would indicate that the reference image and the target image are the same. In other words, a XCR of 1 represents an ideal situation where the images are exactly at the same location and include the same features. Therefore, in the present case, if the cross-correlation coefficient of the reference and target images is less than 1 (XCR<1), it can be determined that motion (difference in position) between the reference and target images exists. As explained in more detail below, the cross-correlation coefficient can be used to calculate a difference in position of one image (target image) with respect to the reference image, and the calculated position can be indicative of an amount of movement (MOV). Therefore, a threshold can be established to determine if the amount of movement is above or below a certain limit of acceptable or non-acceptable movement. Similarly, based on the XCR, an amount of overlap between the target and reference images can be estimated. For example, a low cross-correlation coefficient of substantially 0 (XCR≈0) may be used to determine that there is no overlap between the reference and target images. That is, a low cross-correlation coefficient (below certain level of correlation) may represent a determination that the target image has been acquired outside of the frame of the reference image. Therefore, a threshold can be established in which certain low XCR value between the target and reference images is indicative excessive eye motion or poor quality of estimation of movement.

In addition, eye motion can be determined by evaluating the relative position of image features in the target and reference images. Salient and distinctive features, such as closed-boundary regions, edges, contours, line intersections, corners, etc., in both the reference and target images can be detected and evaluated. For example, in comparing a feature (e.g., bright spot due to diseased tissue cells or the like) in a target frame to a similar feature in the reference frame, the position of the feature pixels in the target image can be compared to that of the reference image. Then, by evaluating the distance in pixels between the location of the specific feature between the target and reference image, the amount of motion (MOV) can be determined, and a decision can be made as to whether the motion is small enough to track and repair (compensate), or excessively large that cannot be compensated. There are other techniques for tracking eye motion. However, most other techniques involve intensive data processing and would require excessive processing time, which is not desirable because lengthy examination would cause stress and discomfort on the subject examinee. Therefore, eye motion tracking techniques that offer fast and efficient detection, as well as accurate correction of motion, are more desirable.

Figure 6A:
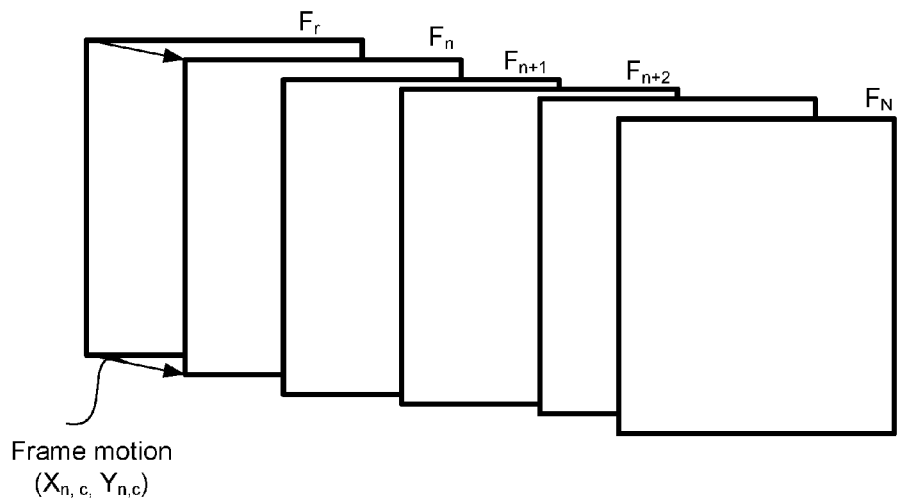
FIG. 6A illustrates an example of full frame motion calculation between a target frame and a reference frame.

Yang et al. (herein "Yang"), in a document entitled "Closed-loop optical stabilization and digital image registration in adaptive optics scanning light ophthalmoscopy" describe an eye motion tracking technique based on cross-correlation of reference and target SLO images. According to Yang, a minimum amount of image data of a target image is required for robust cross-correlation with a reference image. And such minimum amount of data can be obtained from a portion of a frame of the target image, and the obtained portion (e.g., a strip of the target frame) can be used to compare (correlate) with a corresponding portion of the reference image. However, to ensure sufficient overlap between the reference image and the target image, it is convenient to first calculate the full frame motion between the frame being acquired (target frame) and the reference frame (reference image). This is illustrated in FIG. 6, where Fr is the reference frame, Fn is the frame where eye motion is being detected, and Frame Fn+1 is the next frame.

The frame motion (Xn,c, Yn,c) between the reference frame Fr and the target frame Fn being acquired is computed after the entire frame Fn has been acquired, but before beginning the acquisition of the next frame Fn+1 (e.g., before the first strip of next frame Fn+1 is received at the image processor). The frame motion computation can be done during the retrace period of the slow scanner of the SLO apparatus. Specifically, the computer 300 calculates the frame motion (Xn,c, Yn,c) between a target frame Fn and reference frame Fr as a difference between the coordinates (position) of the target frame (Xn, Yn) with respect to those of the reference frame (Xr, Yr)). Then the computer 300 calculates the frame motion between the next target frame Fn+1 and the reference frame Fn from the difference between ((Xn+1,Yn+1)−(Xn,Yn)), and so on.

The following fast Fourier transform based (FFT-based) cross-correlation algorithm as proposed by Yang or other known algorithms can be used for fast computation.

When $r(x,y)$ is the reference image; $t(x,y)$ is the target image; $FFT_{R2C(\ )}$ is the forward 2D real-to-complex FFT operator (this can be implemented by known software, e.g., MatLab®, with the CUDA function cufftExecR2C); $FFT^{-1}_{C2R(\ )}$ is the inverse 2D complex-to-real FFT operator (also implemented with cufftExecR2C); A(u,v), R(u,v), and T(u, v) are the corresponding images in frequency domain, the following expressions hold true:

$$R(u,v)=FFT_{R2C}(r(x,y))$$

$$T(u,v)=FFT_{R2C}(t(x,y))$$

$$A(u,v)=R(u,v)\text{conj}(T(u,v))$$

$$b(x,y)=FFT_{C2R}^{-1}(A(u,v))$$

$$(x,y)_{max}=\arg\max(b(x,y)),$$

where $(x,y)_{max}$ is the translation between the reference image $r(x,y)$ and the target image $t(x,y)$.

Figure 6B:
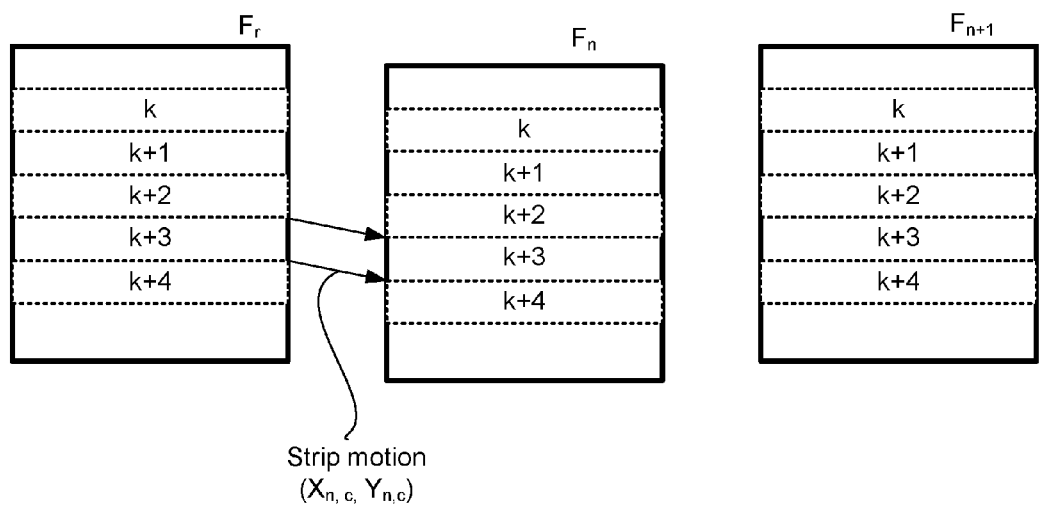
FIG. 6B illustrates an example of strip motion calculation between a strip of a target frame and a strip of a reference frame.

To obtain motion measurements at a frequency greater than the frame rate, which is preferable for real-time optical stabilization and digital image registration, it is convenient to divide each image frame into multiple strips along the direction of the slow scan, as shown in FIG. 6B. In the example shown in FIG. 6B, the fast scan is horizontal and the slow scan is vertical. Therefore, the image frame is divided into horizontal strips. Individual strips are denoted as dash-dot rectangles: k, k+1, k+2, k+3, and k+4. When the motion between frames is small, cross-correlation between two strips with the same index (e.g. strip k+4 in the reference frame Fr and strip k+4 in the target frame Fn) returns the translation of the strip k+4. Therefore, the translation between the k+4 strip of the target frame Fr with respect to the k+4 strip of the reference frame Fn represents the eye motion between the two frames. The same cross-correlation between reference and target images can be implemented using not a strip of the frame, but a predetermined region of a frame. For example, a region having a predetermined amount of pixels centered on a particular feature, such as diseased region of eye recognized in consecutive SLO reference and target images as a bright spot, which can be cropped and used to calculate the cross-correlation coefficient.

The foregoing FFT-based cross-correlation can be applied to both AOSLO images and WFSLO images. However, due to the difference in resolution and scanning speed, the threshold of movement used is different for AOSLO images from that used for WFSLO images.

Turning again to FIG. 3, at step S312, the CPU 301 determines whether the cross-correlation coefficient of a correlation of the target and reference AOSLO images (XCR of small field or $XCR_{SF}$), based on position information A, is equal to or greater than a given threshold value (threshold1). For example, in AOSLO images where the resolution is high and the scanning speed is fast, a high cross-correlation coefficient would be desirable as the value of threshold1, so that image stabilization (correction of movement) can be performed accurately and in a very short time. As noted above, a high XCR value between target and reference images can be indicative of small eye movement or indicative of high accuracy of movement estimation. Therefore, for example, a threshold value of 0.75 or more ($XCR_{SF}>0.75$) may be used as the value of threshold1.

In this manner, if at step S312 ($XCR_{SF}$<threshold1?), the CPU 301 determines that the XCR of the target and reference AOSLO images ($XCR_{SF}$) is less than threshold1 (YES at S312), the process proceeds to step S318.

On the other hand, if at step S312, the CPU 301 determines that the XCR of the target and reference AOSLO images ($XCR_{SF}$) is equal to or greater than threshold1 (NO at step S312), the process advances to step S314. At step S314, since the cross-correlation is higher than the defined threshold1, the CPU 301 determines whether the amount of movement between the target and reference AOSLO images ($MOV_{SF}$) is greater than a movement threshold value (threshold2). Here, the movement threshold value (threshold2) may be a predetermined number of pixels that the target image has moved with respect to the reference image. Similarly, the movement threshold value (threshold2) may be a predetermined percentage (%) of the image size. For example, if the CPU 301 determines that the target AOSLO image has a movement of more than 10 pixels (or more than 5% of the image size) with respect to the reference AOSLO image (YES at step S314), the process proceeds to step S318. The movement threshold value (threshold2) can be determined by various parameters and configurations. For example, a FOV ratio between the AOSLO and WFSLO can be used as the parameter. If the FOV of the AOSLO is 10 times smaller than that of WFSLO, and the pixel number of these images are proportionally the same, 10 pixels of AOSLO equals 1 pixel of WFSLO. In this case, when considering the FOV ratio, the CPU 301 can be programmed to determine whether about more than 20 pixels difference of AOSLO can be detected with reference to the WFSLO image. So the threshold (threshold2) can be 20 pixels for the above example. In another case, if there is a 100 pixel difference between the reference and target frame of a 400 pixel-wide image, the calculation result could not be accurate enough and the result should be handled as being above the threshold even if the XCR is low.

If, at step S314, the CPU 301 determines that the target AOSLO image has a movement value equal to or less than threshold2 (e.g., movement is equal to or less than 10 pixels or equal to or less than 5% of the image size) with respect to the reference AOSLO image (NO at step S314), the process proceeds to step S316.

At step S316, the CPU 301 controls the tracking mirror 319 according to the position calculated at step S310. That is, at step S316, the CPU 301 sends movement data (position information: position A) to the control circuit 30, and the circuit DAC 32 coverts the movement data into voltage signals. Then, the AOSLO control circuit 34 sends the voltage signals to the main scanning mirror (X scanning mirror) of the AOSLO XY scanner 119, and the track control circuit 39 sends the voltage signal to the tracking mirror 319. In response to the received voltage signals, the tracking mirror 319 adjusts (moves) the position of the beam of measurement light 107 on the retina Er to negate the effect of eye motion according to the position A calculated at step S310.

At step S318, since the cross-correlation coefficient between of the target and reference AOSLO images is below threshold1 (or the amount of movement between the target and reference AOSLO images is higher than threshold2), the CPU 301 calculates position information (position B) from a difference in position between the target WFSLO image and the reference WFSLO image. Here, the calculation of position information or frame motion can be done according to the FFT-based cross-correlation algorithm described above in reference to the AOSLO images. However, in the case of WFSLO images, the motion between consecutive WFSLO frames is somewhat different due to the large amplitude motion detected due to the lower resolution and reduced scanning speed of the WFSLO apparatus. Therefore, in addition to FFT-based cross-correlation, some kinds of image filter such as Sobel filter to emphasize edges of structures can be used because WFSLO images usually contain more structures such as blood vessels.

At step S320, based on the amount of movement (position B) calculated at S318, the CPU 301 controls the tracking mirror 319 to negate the movement. That is, at step S320, the CPU 301 sends movement data (position information: position B) to the control circuit 30, and the circuit DAC 32 coverts the movement data into voltage signals. Then, the AOSLO control circuit 34 sends the voltage signals to the main scanning mirror (X scanning mirror) of the AOSLO XY scanner 119 of AOSLO apparatus 100, and the track control circuit 39 sends the voltage signals to the tracking mirror 319. In response to the received voltage signals, the tracking mirror 319 adjusts (moves) the position of the beam of measurement light 107 on the retina Er to negate the effect of eye motion calculated by the difference in position between the target WFSLO image and the reference WFSLO image. Once the tracking mirror 319 has adjusted the position of the beam of measurement light 107 on the retina Er to negate the effect of eye motion, the process proceeds to step S322. Here it should be noted that the track control circuit 39 sends the voltage signals to the tracking mirror 319 in a manner similar to that described in step S316. This assumes the use of a single tracking mirror. However, in other embodiments, at step 320, the track control circuit 39 sends the voltage signals to a tracking mirror to be for operated WFSLO tracking only. That is, it is contemplated that the track control circuit 39 can send the voltage signals to a single tracking mirror 319 (as shown in FIG. 2), or it can send the voltage signals to an AOSLO tracking mirror and a WFSLO tracking mirror.

At step S322, the CPU 301 issues a prompt to the user as to whether the tracking process should be terminated or continued. The prompt may be displayed in output display 304. If the user decides to not end tracking and to continue the tracking process (NO at S322), the flow process returns to step S306 where a new AOSLO target image is acquired, and the remaining process is repeated as desired. If the user decides to end the tracking process (YES at S322), the CPU 301 terminates the flow process at step S324.

FIG. 4 illustrates flow tracking process performed for eye movement tracking and optical stabilization with a modification of the algorithm shown in FIG. 3. In FIG. 4, steps S302 to step S318 are the same as those described above with reference to FIG. 3. However, when the calculated position B (or relative motion between the target WFSLO image and the reference WFSLO image) is greater than a predetermined threshold (threshold3), for example, due to a blink of the eye, the cross-correlation coefficient of the WFSLO images ($XCR_{WF}$) drops below threshold3. The threshold3 may vary from subject to subject, and from system to system, but for the purposes of illustration, threshold3 preferably represents a wide field movement ($MOV_{WF}$) larger than that of threshold2 (e.g., motion greater than 30 or 50 pixels) and a cross-correlation coefficient lower than that of threshold1. For example, a low cross-correlation coefficient of 0.2 to 0.3 may be used as the value of threshold3. Here, a low cross-correlation coefficient threshold3 may be preferred because in clinical imaging situations, particularly when imaging diseased eyes, images have very low contrast and high noise and do not produce correlation coefficients greater than about 0.5 or 0.6. Therefore, if at step S419A, the CPU 301 determines the cross-correlation coefficient of the target and reference WFSLO images ($XCR_{WF}$) is less than threshold3 (YES at S419A), the process proceeds to step S306 where the flow process is repeated, and control is now based on the cross correlation of the target and reference AOSLO images. If at step S419A, the CPU 301 determines the cross-correlation coefficient of the target and reference WFSLO images ($XCR_{WF}$) is equal to or greater than threshold3 (NO at S419A), the process proceeds to step S419B.

At step S419B, the CPU 301 determines whether the amount of movement between the target and reference WFSLO images is greater than a predetermine threshold (threshold4). Here, similar to step S310, the image size or the number of pixels may be used to determine the amount of movement between the target and reference WFSLO images. In addition, instead of calculating movement based on the entire image frame, a strip of the WFSLO image can be used. Therefore, whereas threshold2 determines whether a movement of 10 pixels or 10% of the image size has been detected, threshold4 can be set to a value of motion greater than 30 or 50 pixels, or to a value equal to a 25% of the frame size. In one embodiment, threshold4 can be set based on the size (or maximum number of pixels) of the AOSLO image. In this manner, if the amount of movement between the target and reference WFSLO images is larger than the size of the target or reference AOSLO image, the CPU 301 executes steps S419A and S419B of the algorithm to change the tracking from the WFSLO apparatus back to the AOSLO apparatus. Naturally, the values for threshold4 and threshold3 can be adjusted to tolerate more or less error as required for the particular application.

Therefore, at step S419B, if the CPU 301 determines the amount of movement between the target and the reference WFSLO images ($MOV_{WF}$) is greater than threshold4 (e.g., motion greater than or 50 pixels, or greater than a 25% of the WFSLO frame, or greater than the size of a AOSLO image), the flow proceeds (through YES of S419B) to step S306. At step S306, the flow process is repeated, and control is based on the correlation of the target and reference AOSLO images. If at step S419B, the CPU 301 determines the movement between the target and reference WFSLO images ($MOV_{WF}$) is equal to or less than threshold4 (NO at S419B), the process proceeds to step S420.

At step S420, the CPU 301 controls the tracking mirror 319 and the XY scanner 219 of the WFSLO apparatus 200. Specifically, at step S420, based on the amount of movement (position B) calculated at S318, the CPU 301 controls the tracking mirror 319 and the WFSLO XY scanner 219 to negate the excessive movement determined at S419B. That is, at step S420, the CPU 301 sends movement data (position information: position B) to the control circuit 30, and the circuit DAC 32 coverts the movement data into voltage signals. Then, the WFSLO control circuit 35 sends the voltage signals to the main scanning mirror (X scanning mirror) of the XY scanner 219 of the WFSLO apparatus 200, and the track control circuit 39 sends the voltage signals to the tracking mirror 319. In response to the received voltage signals, the tracking mirror 319 adjusts (moves) the position of the beam of measurement light 207 on the retina Er to negate the effect of eye motion calculated by the difference in position between the target WFSLO image and the reference WFSLO image. Once the position of the beam of measurement light 207 on the retina Er has been corrected, the process proceeds to step S322. Steps S322 and S324 are similar to those described with reference to FIG. 3.

FIG. 5 illustrates another flow process for eye movement tracking and stabilization with a further modification of the flow process of FIG. 3. According to FIG. 5, the CPU 301 executes steps S302 to S310 in the same manner as in FIG. 3. In addition, after step S310, the CPU 301 executes step S318 also in the same manner as described above in reference to FIG. 3. However, at step S414, the CPU 301 determines whether position information calculated from AOSLO images (position A) matches well or substantially coincides with position information calculated from WFSLO images (position B). At step S414, if the position information calculated from AOSLO images (position A) matches well or substantially coincides with position information calculated from WFSLO images (position B), YES at S414, the CPU 301 controls the tracking mirror 319 in the same manner as is step S316. Basically position A indicated in microns or degrees should be same as position B indicated in microns or degrees. As pixel resolution should be predetermined in both AOSLO and WFSLO images, position A and position B can be calculated in microns of degrees. If the position information calculated from AOSLO images (position A) does not match well or is not within a reasonable degree of agreement with position information calculated from WFSLO images (position B), NO at S414, the CPU 301 controls the tracking mirror 319 according to position B alone, in the same manner as in step S320 already described above. Steps S322 and S324 are similar to those described with reference to FIG. 3.

In FIG. 5, for example, a reasonable degree of agreement, "match", or overlap between position A and position B may be considered if the CPU 301 determines that both the cross-correlation coefficient of the AOSLO images ($XCR_{SF}$) and the cross-correlation coefficient of the WFSLO images ($XCR_{WF}$) are both above 0.95, and/or differ by no more than 5%. Alternatively, the CPU 301 can be programmed to determine that position A substantially matches with position B if an amount of movement between target and reference AOSLO images as well as between target and reference WFSLO images is below a percentage (e.g., 5%) of the image size, or an amount of movement thereof is no more than a few pixels (e.g., 2 pixels or less).

FIG. 7 shows another embodiment in which tracking control of the tracking mirror is based on position information calculated from WFSLO images only, and a process for determining whether calculated movement is accurate or inaccurate. In the process of FIG. 7, the CPU 301 executes step S704 to obtain a WFSLO reference image (WFSLO Ref), step S708 to obtain a WFSLO target image (WFSLO Trg), and step S710 to calculate position information of WFSLO target image with respect to the WFSLO reference image. The steps S704 to S710 are executed in the same manner as steps S304, S308, and S318 of FIG. 3. Therefore, description of S704, S708, and S710 is omitted for the sake of brevity. After calculating the position information (position information B) of the WFSLO target image with respect to the WFSLO reference image, the CPU 301 determines whether the calculated movement (based on position information B) is accurate by executing steps S712, S714, and S715.

At step S712, the CPU 301 determines if the cross-correlation coefficient of a correlation between the target and reference WFSLO images is low. That is, the CPU 301 determines if the cross-correlation coefficient of the WFSLO images ($XCR_{WF}$) is below a user-established threshold (thresholdA). For example, a low cross-correlation coefficient of 0.2 to 0.3 may be used as the value of thresholdA. A low cross-correlation coefficient for thresholdA may be preferred because in clinical imaging situations, particularly when imaging diseased eyes, images tend to have very low contrast and high noise and do not produce correlation coefficients greater than 0.5 to 0.6. Naturally, these values are exemplary, and can be adjusted according to the imaging application. Therefore, this step S712 is executed in a manner similar to step S419A.

At step S712, if the CPU 301 determines the cross-correlation coefficient of the target and reference WFSLO images ($XCR_{WF}$) is less than a predetermined thresholdA (YES at S712), the CPU 301 determines the cross-correlation coefficient ($XCR_{WF}$) is too low, and the process proceeds to step S718. If at step S712, the CPU 301 determines the cross-correlation coefficient of the target and reference WFSLO images ($XCR_{WF}$) is equal to or greater than the thresholdA (NO at S712), the process proceeds to step S714.

At step S714, the CPU 301 determines whether the calculated eye motion is too large. Therefore, this step S714 is similar to step S419B. At step S714, the CPU 301 determines whether the amount of movement between the target and reference WFSLO images ($MOV_{WF}$) is greater than a predetermine threshold (thresholdB). Here, similar to steps S310 and S419B, the image size or the number of pixels may be used to determine the amount of movement of the WFSLO target with respect to the WFSLO reference image. Therefore, the value of thresholdB can be set to a value of motion greater than 30 or 50 pixels, or a 25% of the frame size, for example.

At step S714, if the CPU 301 determines the amount of movement between the target and the reference WFSLO images ($MOV_{WF}$) is greater than thresholdB, the flow proceeds (through YES of S714) to step S718. If at step S714, the CPU 301 determines the movement between the target and reference WFSLO images ($MOV_{WF}$) is equal to or less than thresholdB (NO at S714), the process proceeds to step S715.

At step S715, the CPU 301 determines whether calculated movement is less than the optical resolution or is near the optical resolution. Specifically, the CPU 301 determines whether the movement between the target and reference WFSLO images ($MOV_{WF}$) is equal to or less than the optical resolution. The optical resolution is a parameter determined by the wavelength of the measurement light and the diameter of the incident light at the subjects' pupil. In general, a WFSLO apparatus has about 20 microns optical resolution for a 1 mm pupil diameter when measured with a 900 nm light source. Therefore, at step S715, if the CPU 301 calculates a movement between the target and reference WFSLO images ($MOV_{WF}$) equal to or less than 20 microns, the CPU 301 determines the calculated movement is less than the optical resolution (YES at S715) and therefore it is inaccurate. In this case, the flow proceeds to step S718. If, at step S715, the CPU 301 determines the calculated movement is greater than the optical resolution (NO at S715), the flow proceeds to step S716.

At step S716, if the CPU 301 determines that the calculated movement ($MOV_{WF}$) is judged accurate, that is, the correlation coefficient ($XCR_{WF}$) is not less than thresholdA (NO at S712), the movement is not larger than a predetermined thresholdB (NO at S714), and not less that the optical resolution (NO at S715), the CPU 301 controls the WFSLO XY scanner 219 and controls the tracking mirror 319 based on the calculated position information (position B). Subsequently, at step S718, the CPU 301 controls the AOSLO XY scanner 119 to acquire an AOSLO image.

On the other hand, if the CPU 301 determines that the calculated movement of WFSLO target image with respect to the WFSLO reference image is judged inaccurate, the CPU 301 does not move the tracking mirror. That is, if the cross-correlation coefficient is too low as compared to threshold (YES at S712), the movement is excessively large as compared to thresholdB (YES at S714), and/or the movement is less than the optical resolution (YES at S715), the CPU 301 determines that the calculated movement between target and reference WFSLO images is judged inaccurate, and does not move the tracking mirror. Instead, at step S718, the CPU 301 controls the AOSLO XY scanner 119 to obtain the AOSLO image without adjusting for movement; that is, without using the tracking mirror 319. At step S720, the CPU 301 issues a prompt to the user thereof as to whether the tracking process should be ended. The user controls the ophthalmic apparatus 80 as to whether to end the tracking process (S720:YES, S722) or continue the tracking process (S720:NO). In the case that the user decides to continue the tracking process, the CPU 301 returns the flow process to step S708 where a new WFLSO target image is acquired, and the process repeats according to the flow. In the case that the user decides to end the tracking process, the CPU 301 stops the process at S722.

In the foregoing description, SLO reference and target images are acquired by either the AOSLO apparatus 100 or the WFSLO apparatus 200. Those skilled in the art will appreciate that the WFSLO apparatus can be replaced by other optically equivalent imaging apparatus capable of acquiring wide field images. For example, any one of a fundus camera, mydriatic camera, or an OCT apparatus may be used instead of the WFSLO apparatus.

Certain embodiments or processes of the present invention can be realized by a computer of a system or processing apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). An example is described as computer 300 including a processor (CPU 301). However, the computer 300 may comprise one or more central processing units, a micro processing unit (MPU), or other circuitry, and may include a network of separate computers or separate computer processors. The computer executable instructions may be provided to the computer, for example, from a network or may be loaded onto a storage medium. The storage medium may include, for example, one or more of a hard disk (illustrated as HDD 302, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An opthalmological apparatus comprising:
a first acquiring unit configured to acquire a reference AOSLO (Adaptive Optics Scanning Laser Ophthalmoscope) image and a reference WFSLO (Wide Field Scanning Laser Ophthalmoscope) image of an eye to be examined;
a second acquiring unit configured to acquire a target AOSLO image and a target WFSLO image of the eye to be examined, and
a processor configured to calculate a position of the target AOSLO image with respect to the reference AOSLO image,
wherein, in a case where the position of the target AOSLO image with respect to the reference AOSLO image differs by more than a first threshold, the processor calculates a position of the target WFSLO image with respect to the reference WFSLO image, and the processor controls an AOSLO tracking mirror according to a difference in position of the target WFSLO image with respect to the reference WFSLO image.

2. The apparatus according to claim 1, wherein, in a case where the position of the target AOSLO image with respect to the reference AOSLO image differs by less than the first threshold, the processor controls the AOSLO tracking mirror according to a difference in position of the target AOSLO image with respect to the reference AOSLO image.

3. The apparatus according to claim 1, wherein, in a case where the position of the target AOSLO image with respect to the reference AOSLO image and the position of the target WFSLO image with respect to the reference WFSLO image match, the processor controls the AOSLO tracking mirror according to the position of the target AOSLO image with respect to the reference AOSLO image.

4. The apparatus according to claim 1, wherein, in a case where the position of the target AOSLO image with respect to the reference AOSLO image and the position of the target WFSLO image with respect to the reference WFSLO image do not match, the processor controls the AOSLO tracking mirror according to the position of the target WFSLO image with respect to the reference WFSLO image.

5. The apparatus according to claim 1, wherein, in a case where a value of a cross-correlation coefficient of a correlation of the target AOSLO image with the reference AOSLO image is greater than the first threshold, the processor controls the AOSLO tracking mirror according to an amount of movement of the target AOSLO image with respect to the reference AOSLO image.

6. The apparatus according to claim 5, wherein, in a case where the amount of movement is larger than a movement threshold, the processor controls the AOSLO tracking mirror according to the position of the target WFSLO image with respect to the reference WFSLO image.

7. The apparatus according to claim 5, wherein, in a case where the amount of movement is equal to or less than a movement threshold, the processor controls the AOSLO tracking mirror according to an amount of movement corresponding to a cross-correlation coefficient of a correlation of the target AOSLO image with the reference AOSLO image.

8. The apparatus according to claim 5, wherein, in a case where the amount of movement is larger than a movement threshold, the processor controls a WFSLO tracking mirror according to the position of the target WFSLO image with respect to the reference WFSLO image.

9. The apparatus according to claim 1, wherein, in a case where an amount of movement of target AOSLO image with respect to the reference AOSLO image is larger than a movement threshold, the processor controls a WFSLO tracking mirror according to one of a cross-correlation coefficient of a correlation of the target WFSLO image with the reference WFSLO image or an amount of movement of the target WFSLO image with respect to the reference WFSLO image.

10. A method of imaging an area of an eye of a subject, the method comprising:
providing a light from a light source;
a scanning step of scanning the light by scanners to scan the light on a scanning area;
an image constructing step of constructing an image with light from the scanning area of the subject;
a reference image setting step of setting an image of the subject as a reference;
a position detecting step of detecting a relative change in a position of the scanning area on the subject by comparing the reference image and constructed image;
an imaging area controlling step of controlling the scanning area according to the detected relative change in the position of the scanning area;
an evaluation step to check accuracy of the position detection and change the controlling method according to the accuracy.

11. The method of claim 10, wherein the imaging area controlling step includes changing control gain according to the accuracy.

12. The method of claim 10, wherein the evaluation step includes determining accuracy by calculating a cross correlation coefficient of the reference image and a part of the target image.

13. The method of claim 10, wherein the evaluation step includes determining accuracy by calculating a cross correlation coefficient of the reference image and the target image.

14. The method of claim 10, wherein the evaluation step includes determining accuracy by comparing the calculated position information and a preset limit.

15. The method of claim 10, wherein the evaluation step includes determining accuracy by comparing the position information calculated from small area images and the position information calculated from large area images.

16. The apparatus according to claim 15, wherein a resolution of the small area images is higher than a resolution of the large area images.

17. The apparatus according to claim 16, wherein the small area images are AO images and the large area images are WF images.

18. The method of claim 10, wherein the evaluation step includes determining accuracy by comparing the position and the optical resolution of the light on the subject.

19. A method of imaging an area of a subject, the method comprising:
providing a light from a light source;
a scanning step of scanning the light by scanners to scan the light on a scanning area;
an image constructing step of constructing an image with light from the scanning area of the subject;
a reference image setting step of setting an image of the subject as a reference;
a position detecting step of detecting a relative change in a position of the scanning area on the subject by comparing the reference image and constructed image;
a large area scanning step and large area image constructing step;
a large movement detecting step comparing large area reference image and large constructed image;
an imaging area controlling step controlling the scanning area according to the detected relative change in the position of the scanning area;
an evaluation step to check accuracy of the position detection of each position calculation step and switch position data to control the scanning area in the imaging area controlling step according to the accuracy.

20. The apparatus according to claim 19, wherein the reference image and the constructed image are AO images and the large area reference image and large constructed image are WF images.

21. An ophthalmic apparatus comprising:
a first acquiring unit configured to acquire a reference AO (Adaptive Optics) image and a target AO image of an eye to be examined;
a second acquiring unit configured to acquire a reference WF (Wide Field) image and a target WF image of the eye to be examined;
a calculation unit configured to calculate first position information of the target AO image with respect to the reference AO image and second position information of the target WF image with respect to the reference WF image; and
a control unit configured to control an acquiring position of the target AO image on the eye to be examined according to the first position information or the second position information based on a predetermined condition.

22. The apparatus according to claim 21, wherein, in a case where the first position information differs by more than a first threshold, the control unit control the acquiring position according to the second position information, and in a case where the first position information differs by less than the first threshold, the control unit control the acquiring position according to the first position information.

23. The apparatus according to claim 21, wherein, in a case where the first position information and the second position information match, the control unit control the acquiring position according to the first position information, and in a case where the first position information and the second position information do not match, the control unit control the acquiring position according to the second position information.

24. The apparatus according to claim 21, wherein, in a case where a value of a cross-correlation coefficient of the target AO image with the reference AO image is greater than a first threshold, the control unit control the acquiring position according to an amount of movement of the target AO image with respect to the reference AO image, and in a case where the value is equal to or less than the first threshold, the control unit control the acquiring position according to an amount of movement of the target WF image with respect to the reference WF image.

25. The apparatus according to claim 21, wherein the control unit control, according to the first position information or the second position information, a tracking mirror configured to correct the acquiring position on the eye to be examined.

26. The apparatus according to claim 21, further comprising
a memory that stores a program; and
a processor that executes the program stored in the memory so as to function as the calculation unit and the control unit.

27. The apparatus according to claim 21, wherein the calculation unit and the control unit are implemented using a processor.

28. The apparatus according to claim 21, wherein the first acquiring unit comprises a scanner that scans light on the eye to be examined,
wherein the acquiring position is a position on the eye irradiated with a beam spot of the light scanned by the scanner.

29. A method for controlling an ophthalmic apparatus, the method comprising:
acquiring a reference AO (Adaptive Optics) image and a target AO image of an eye to be examined;
acquiring a reference WF (Wide Field) image and a target WF image of the eye to be examined;
calculating first position information of the target AO image with respect to the reference AO image and second position information of the target WF image with respect to the reference WF image; and
controlling an acquiring position of the target AO image on the eye to be examined according to the first position information or the second position information based on a predetermined condition.

* * * * *